(12) United States Patent
Toyoshima et al.

(10) Patent No.: US 8,129,192 B2
(45) Date of Patent: Mar. 6, 2012

(54) METHOD FOR ANALYZING DITHIOCARBAMATE PESTICIDE USING MICROWAVE-ASSISTED THERMAL DIGESTION AND EXTRACTION

(75) Inventors: Takahiro Toyoshima, Ibaraki (JP); Akiko Kido, Ibaraki (JP)

(73) Assignee: Tsumura & Co., Tokyo (JP)

( * ) Notice: Subject to any disclaimer, the term of this patent is extended or adjusted under 35 U.S.C. 154(b) by 19 days.

(21) Appl. No.: 12/670,295

(22) PCT Filed: Jun. 20, 2008

(86) PCT No.: PCT/JP2008/061329
§ 371 (c)(1),
(2), (4) Date: Jan. 22, 2010

(87) PCT Pub. No.: WO2009/016897
PCT Pub. Date: Feb. 5, 2009

(65) Prior Publication Data
US 2010/0210020 A1    Aug. 19, 2010

(30) Foreign Application Priority Data
Jul. 27, 2007 (JP) ................................ 2007-195853

(51) Int. Cl.
*G01N 33/00* (2006.01)
*G01N 1/18* (2006.01)

(52) U.S. Cl. ........ 436/119; 436/106; 436/161; 436/174; 436/175; 436/178

(58) Field of Classification Search .................. 436/106, 436/119, 120, 161, 174, 175, 177, 178, 81
See application file for complete search history.

(56) References Cited

FOREIGN PATENT DOCUMENTS

JP    2008-064670    *    3/2008

OTHER PUBLICATIONS

Perz, et al., "High Performance I on Pair 1-7 Chromatography as a Routine-compliant Tool for surveilling Residue•s of Dithiocarbamate Fungicides i n Fruits and Vegetables.", Dtsch Lebensm Runds, 2003, vol. 99(4):137-142.
Vryzas, et al., "Microwave-Assisted Extraction (MAE). Acid Hydrolysis of Dithiocarbamates for Trace Analysis in Tobacco and Peaches.", J. Agric. Food Chem., 2002, vol. 50(8):2220-2226.
Kobayashi, et al., "Effect of Cysteine on the Stability of Ethylenethiourea and. Ethylenebis(dithiocarbamate) in Crops during Storage and/or Analysis.", J. Agric. Food Chem., 1992, 40:76-80.
Toyoshima, et al., "A-7 Examination of Simple Analysis Method for Residual Dithiocarbamate Pesticides.", 95th Academic Lecture Meeting of the Japanese Society for Food Hygiene and Safety, May 15-16, 2008.

* cited by examiner

*Primary Examiner* — Maureen Wallenhorst
(74) *Attorney, Agent, or Firm* — Lucas & Mercanti, LLP

(57) ABSTRACT

A method for analyzing a dithiocarbamate pesticide is provided. The method includes the steps of: adding a crude drug, a preparation containing the same, or a treated product thereof, an aqueous acid catalyst solution, L-cysteine or a salt thereof, and an organic solvent for extraction to a reaction vessel, sealing the vessel, carrying out microwave irradiation, digesting a dithiocarbamate pesticide existing in the crude drug or the preparation containing the same into carbon disulfide, carrying out fractional extraction using the above organic solvent, and then analyzing the extract.

19 Claims, No Drawings

METHOD FOR ANALYZING DITHIOCARBAMATE PESTICIDE USING MICROWAVE-ASSISTED THERMAL DIGESTION AND EXTRACTION

This application is a 371 of PCT/JP2008/061329 filed on Jun. 20, 2008, which claims the benefit of Japanese Patent Application No. 2007-195853 filed on Jul. 27, 2007,the contents of each of which are incorporated herein by reference.

TECHNICAL FIELD

The present invention relates to a method for analyzing a dithiocarbamate pesticide in a sample.

BACKGROUND ART

Dithiocarbamate pesticides are broadly used as antimicrobial agents or nematicides in the fields of pesticides and are also used in fields involving medicinal crude drugs that are raw materials for kampo preparations.

A carbon disulfide method (that is, a typical method for analyzing a dithiocarbamate pesticide) is a technique that involves heating a dithiocarbamate pesticide remaining in a sample in an acid catalyst, digesting it into carbon disulfide, measuring the level of carbon disulfide, and then quantitatively determining the level of the residual pesticide in terms of carbon disulfide. This method requires the use of special glassware for digestion and various powerful drugs (hydrochloric acid, concentrated sulfuric acid, and alkali) and is complicated as an analytical method. Another example is a methylation method that involves derivatizing a dithiocarbamate pesticide and then quantitatively determining the derivative. Such methylation method is better than the carbon disulfide method since it allows species of residual pesticides (ethylenebisdithiocarbamates, dimethyldithiocarbamates, and propylenebisdithiocarbamates) to be determined, but is almost the same as the carbon disulfide method in terms of maneuverability and ability for specimen treatment. Also, because of the physical properties (degradability and poor solubility) of dithiocarbamate pesticides, it is difficult to apply thereto a simultaneous analytical method that has generally been employed in recent years and enables simultaneous confirmation of many residual pesticides.

Although the amounts of dithiocarbamate pesticides used are high, there is no choice but to depend on a separate analytical method with poor efficiency of residue analysis because of the above reasons. Hence, residual pesticide control has been considered to be difficult in the case of dithiocarbamate pesticides.

J. Agric. Food Chem., 2002, 50, 2220-2226 discloses a method that involves heating by microwave irradiation a dithiocarbamate pesticide remaining in dry tobacco or peach, so as to digest it into carbon disulfide and then quantitatively determining the carbon disulfide. This analytical method is an extremely simple technique comprising: adding a specimen, 5 mol/L hydrochloric acid, tin (II) chloride as a catalyst, and isooctane as an organic solvent into a resin cylinder, sealing the cylinder, heating the cylinder using microwaves, so as to digest the remaining dithiocarbamate pesticide into carbon disulfide, carrying out fractional extraction using an organic solvent within a reaction cylinder, collecting the organic solvent phase, and then analyzing it using a gas chromatograph (GC-FPD) provided with a flame gas photometric detector.

However, when the present inventors applied the analytical method as described in J. Agric. Food Chem., 2002, 50, 2220-2226 to crude drugs, kampo preparations, and the like, the addition and recovery test for pesticides yielded insufficient results suggesting a need of further improvement.

J. Agric. Food Chem., 1992, 40, 76-80 describes that L-cysteine prevents digestion of mancozeb (manzeb), which is an ethylenebisdithiocarbamate pesticide into ethylenethiourea. However, the document mentions nothing about digestion of an ethylenebisdithiocarbamate pesticide, a propylenebisdithiocarbamate pesticide, or a dimethyldithiocarbamate pesticide into carbon disulfide.

Lecture Summaries of the 29$^{th}$ Pesticide Residue Analysis Committee, 2006, pp. 168-171 describes that: when fruit or vegetable samples are ground, dithiocarbamate pesticides are immediately digested through their contact with fluids; and when L-cysteine is added to such samples, digestion of dithiocarbamate pesticides is suppressed. However, the document does not clarify what kind of degradation reaction is suppressed and suggests nothing about how L-cysteine acts when it is caused to coexist in the microwave-assisted system for digestion reaction of dithiocarbamate pesticides into carbon disulfide. Also, in Lecture Summaries of the 29$^{th}$ Pesticide Residue Analysis Committee, 2006, pp. 168-171, the effects of L-cysteine have been confirmed for *Citrus natsudaidai*, grape, apple, and lettuce samples, but not confirmed for grape tomato samples.

DISCLOSURE OF THE INVENTION

Object to Be Attained by the Invention

An object of the present invention is to provide a method for analyzing a dithiocarbamate pesticide, which can ensure analytical precision with both ease and promptness.

Means for Attaining the Object

The present invention is as summarized as follows.
(1) A method for analyzing a dithiocarbamate pesticide, comprising adding a crude drug, a preparation containing the crude drug, or a treated product thereof, L-cysteine or a salt thereof, and an organic solvent for extraction to a reaction vessel, sealing the reaction vessel, carrying out microwave irradiation, digesting a dithiocarbamate pesticide existing in the crude drug or the preparation containing the same into carbon disulfide, carrying out fractional extraction using the organic solvent, and then analyzing the extract.
(2) The method according to (1) above, comprising further adding an aqueous acid catalyst solution to a reaction vessel and then sealing the vessel.
(3) The method according to (2) above, wherein the aqueous acid catalyst solution contains tin (II) chloride or a hydrate thereof and hydrochloric acid.
(4) The method according to any one of (1) to (3) above, wherein the organic solvent for extraction is cyclohexane or 2,2,4-trimethylpentane.
(5) The method according to any one of (1) to (4) above, whereby analysis is conducted using a gas chromatograph.
(6) The method according to any one of (1) to (5) above, wherein the dithiocarbamate pesticide contains propineb.
(7) The method according to any one of (1) to (6) above, wherein the crude drug or the preparation containing the crude drug is a crude drug, a kampo preparation, a dietary supplement, a quasi-drug, or a cosmetic.

Effects of the Invention

According to the present invention, simultaneous, safe, and rapid treatment of many specimens becomes possible. Therefore, the present invention realizes highly convenient analysis of dithiocarbamate pesticides, which has been a complicated process.

BEST MODES FOR CARRYING OUT THE INVENTION

The method for analyzing a dithiocarbamate pesticide of the present invention is devised by utilizing and improving the principle of a carbon disulfide method that is a dithiocarbamate pesticide analytical method. This technique accelerates pesticide digestion not by direct heating using a mantle heater or the like, but by indirect heating by microwave irradiation. Moreover, this technique involves fractional extraction of the thus degraded and generated carbon disulfide using an organic solvent, measuring the same using a gas chromatograph or the like, and then quantitatively determining the pesticide residue level in terms of carbon disulfide.

A dithiocarbamate pesticide to be analyzed in the present invention is not limited, as long as it is a pesticide having a dithiocarbamate structure represented by the following formula: >N—CS—S—, such as (I), (II), or (III) below:

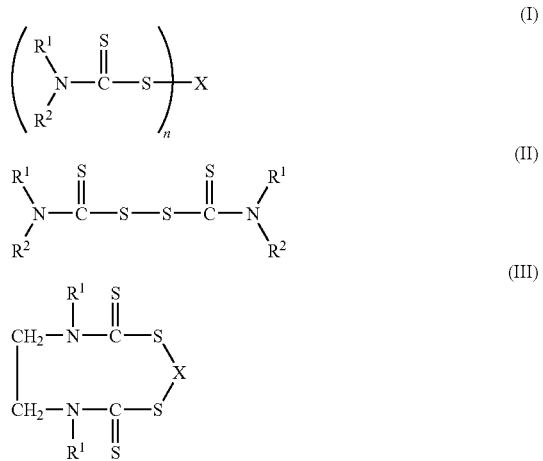

(wherein. $R^1$ and $R^2$ are the same or different and each represent a hydrogen atom, a substituted or unsubstituted phenyl group, a substituted or unsubstituted $C_{1-5}$-alkyl group, a substituted or unsubstituted $C_{3-7}$-alkyl group, an amino group, or a benzothiazolyl group; $R^1$ and $R^2$ may also represent in conjunction with each other a $C_{1-4}$ alkylene group; n represents 1 or 2; and X represents a hydrogen atom, an ammonium group, or a metal atom.).

Examples of a $C_{1-5}$-alkyl group represented by $R^1$ or $R^2$ in the above formula include a methyl group, an ethyl group, an n-propyl group, an isopropyl group, an n-butyl group, an isobutyl group, a sec-butyl group, a tert-butyl group, and an amyl group. An example of a $C_{3-7}$-alkyl group in the above formula is a cyclohexyl group. A phenyl group, a $C_{1-5}$-alkyl group, or a $C_{3-7}$-alkyl group represented by $R^1$ or $R^2$ may be substituted with a dithiocarbamoyl group.

Examples of a metal atom represented by X include alkali metal atoms such as sodium and potassium; alkaline-earth metal atoms such as calcium and magnesium; zinc, nickel, cadmium, iron, copper, manganese, and arsenic.

Specific examples of the above dithiocarbamate pesticide include zineb, maneb, manzeb, ambam, polycarbamate (bis-dimethyldithiocarbamoylzincethylenebisdithiocarbamate), organic nickel (nickel dimethyldithiocarbamate), ferbam, propineb, metiram, ziram, thiuram, and sodium methyldithiocarbamate.

Samples applicable to the present invention are not particularly limited, as long as they are crude drugs or preparations containing the same, or treated products thereof, which are suspected of containing residual dithiocarbamate pesticides. Examples of such samples include crude drugs, kampo preparations, dietary supplements, quasi drugs (e.g., toothpaste), cosmetics, agricultural crops, and soil. Crude drugs or preparations containing the same may be subjected to treatment such as grinding or cutting, if necessary.

In the present invention, an aqueous solution containing L-cysteine or a salt thereof is used. Examples of such salt of L-cysteine include hydrochloride and a hydrate thereof. The concentration of L-cysteine or a salt thereof in the aqueous solution generally ranges from 0.1 w/v % to 10.0 w/v %, ranges from 2.0 w/v % to 6.0 w/v % in analysis of crude drugs, and is preferably 4.0% w/v %.

When the concentration of L-cysteine or a salt thereof is less than 2%, the result is insufficient in terms of recovery percentage. When the concentration of the same is higher than 10%, the viscosity of the reaction solution is increased and the uniformity of the solution is lowered. This results in an insufficient digestion reaction into carbon disulfide.

In the present invention, an aqueous acid catalyst solution may be used together with an aqueous solution containing L-cysteine or a salt thereof, if necessary. Examples of such aqueous acid catalyst solution to be used herein include an aqueous solution containing tin (II) chloride or a hydrate thereof and hydrochloric acid and an acid aqueous solution of sulfuric acid, phosphoric acid, p-toluenesulfonic acid, or the like. Tin (II) chloride or a hydrate thereof, hydrochloric acid, and water may be separately added to a reaction vessel. Alternatively, an aqueous solution is prepared in advance by mixing tin (II) chloride or a hydrate thereof, hydrochloric acid, and water, and furthermore, if necessary, L-cysteine or a salt thereof, and then the thus-obtained aqueous solution may be added to a reaction vessel.

Tin (II) chloride is used as a nonhydrate or a hydrate of a dihydrate or the like. An example of a salt of L-cysteine is hydrochloride or a hydrate thereof.

When an aqueous solution containing tin (II) chloride or a hydrate thereof, hydrochloric acid, and L-cysteine or a salt thereof is prepared in advance, the concentration of hydrochloric acid in the aqueous solution generally ranges from 0.5 mol/L to 6.0 mol/L, the concentration of tin (II) chloride or a hydrate thereof in the same generally ranges from 0.1 w/v % to 5.0 w/v %, and the concentration of L-cysteine or a salt thereof in the same generally ranges from 0.1 w/v % to 5.0 w/v %.

Preferable organic solvents for extraction are generally nonpolar or weakly polar, solvents. Specifically, hexane, heptane, octane, nonane, isooctane (2,2,4-trimethylpentane; the same applies to the following), toluene, and the like in terms of microwave transparency and selectivity for extraction. Cyclohexane and isooctane are particularly preferable in terms of recovery percentage.

A reaction vessel to be used herein is not particularly limited, as long as it is designed to withstand pressure, allows temperature control, and can be sealed. Material of such reaction vessel is not particularly limited, as long as it is a microwave-transparent reaction vessel. Examples of such material include a fluorocarbon polymer (e.g., Teflon or PFA) and glass (e.g., Pyrex™ or quartz).

In general, 0.1 g to 5 g of a sample (a crude drug, a preparation containing the same, or a treated product thereof), 10 mL to 30 mL of an aqueous acid catalyst solution containing L-cysteine or a salt thereof (or an aqueous solution containing L-cysteine or a salt thereof), and 5 mL to 20 mL of an organic solvent for extraction are added per 70-mL reaction vessel. These values are varied depending on the scale of an apparatus to be used herein and can be specifically and adequately varied depending on the size of a microwave irradiation apparatus, microwave power, and a reaction vessel.

After being sealed, the reaction vessels are placed in a microwave-assisted solvent extractor and then the reaction vessels are heated by microwave irradiation from outside the vessels. Microwave heating employs an induction heating method using electromagnetic waves ranging from 300 MHz to 300 GHz. Microwave heating is based on ionic current existing in a medium and dipole rotation of molecules, which is caused by electromagnetic waves.

Microwave irradiation is generally carried out with 15 to 30 minutes of continuous or intermittent irradiation, while the power is maintained at a level between 10 W and 100 W per reaction vessel and the temperature is maintained between 80° C. and 100° C.

In the present invention, microwave irradiation is carried out via the following 3 steps, for example.

To keep the temperature of a reaction solution within the above range, microwave power is increased upon initiation of microwave irradiation, so as to immediately raise the temperature. ($1^{st}$ step)

When the temperature of the solution reaches the above range, microwave power is controlled to a degree such that the temperature can be maintained and then irradiation is carried out for required time length. ($2^{nd}$ step)

After completion of microwave irradiation, the temperature of the reaction solution is lowered to room temperature. ($3^{rd}$ step)

A microwave-assisted solvent extractor to be used herein is not particularly limited, as long as many reaction vessels can be assembled and positioned at the same time so that many specimens can be treated simultaneously. Examples thereof include those produced by Milestone Inc., such as a rotor for simultaneous treatment of multiple specimens (24 vessels) and a torque wrench-tightened 12 rotor. The torque wrench-tightened 12 rotor is preferable in terms of its high ability to withstand pressure.

After completion of digestion reaction, dithiocarbamate pesticides in samples can be analyzed through analysis using various analytical means such as a gas chromatograph and preferably a gas chromatograph with a flame photometric detector (GC-FPD).

Simultaneous, safe, and rapid treatment of many specimens becomes possible by placing many digestion reaction vessels in a microwave oven and then carrying out microwave irradiation.

EXAMPLES

Hereafter, the present invention is described in detail with reference to Examples, although the scope of the present invention is not limited thereto.

Example 1

Addition and Recovery Test for Thiuram, Manzeb, and Propineb in Crude Drugs Using a 4.0% Aqueous L-Cysteine Hydrochloride Solution as a Catalyst Test Solution An addition and recovery test was conducted for 3 kinds of dithiocarbamate pesticides (thiuram, zineb, and propineb) in crude drugs using specimens, analyzers, analysis conditions, and operations as described below.

(1) Specimens, Reagents, and Others (a) Specimens

The following 20 kinds of crude drugs were used as specimens in their original forms or used as specimens after they had been cut, ground, or the like to portions about 3 mm to 5 mm each.

Japanese Angelica Root, *Cnidium* Rhizome, Moutan Bark, Bitter Orange Peel (Tohi), *Citrus Unshiu* Peel, *Pinellia* Tuber, *Bupleurum* Root, *Asiasarum* Root, *Dioscorea* Rhizome, *Polygala* Root, Jujube, Immature Orange, *Schisandra* Fruit, *Achyranthes* Root, *Ophiopogon* Tuber, *Angelica Dahurica* Root, *Perilla* Herb, *Zanthoxylum* Fruit, Common Wheat Seed, and Loquat Leaf (b) Reagents Test Solutions L-cysteine hydrochloride monohydrate: Wako Pure Chemical Industries, Ltd., and special grade reagent 2,2,4-trimethylpentane (isooctane): Kanto Chemical Co., Inc., and extra pure Acetone: Kanto Chemical Co., Inc., for testing residual pesticides Distilled water (washed with hexane): Wako Pure Chemical Industries, Ltd., for testing residual pesticides (c) Catalyst Test Solution Aqueous 4.0% cysteine hydrochloride solution: L-cysteine hydrochloride monohydrate (20 g) was dissolved in distilled water to 500 mL.

(d) Pesticides Tested

Pesticide Reference Standard

Carbon disulfide: Wako Pure Chemical Industries, Ltd., special grade reagent, and reagent purity 99%

Thiuram reference standard: Wako Pure Chemical Industries, Ltd., pesticide reference standard, and reagent purity 100%

Propineb reference standard: GL Sciences Inc., pesticide reference standard, and reagent purity 80% or higher Manzeb reference standard: Wako Pure Chemical Industries, Ltd., pesticide reference standard, and reagent purity 91%

Preparation of Pesticide Standard Solution

Thiuram standard solution (80 µg/mL (in terms of carbon disulfide) solution): Thiuram (3.16 mg) was weighed and then acetone was added thereto, so as to accurately prepare 25 mL of the thiuram standard solution.

Propineb standard solution (80 µg/mL (in terms of carbon disulfide) solution): Propineb (4.75 mg) was weighed, distilled water was added thereto, and then ultrasonic irradiation was carried out to prepare a suspended solution, so as to accurately prepare 25 mL of the propineb standard solution.

Manzeb standard solution (80 µg/mL (in terms of carbon disulfide) solution): Manzeb (3.89 mg) was weighed, distilled water or acetonitrile was added thereto, and then ultrasonic irradiation was carried out to prepare a suspended solution, so as to accurately prepare 25 mL of the Manzeb standard solution.

(e) Pesticides Added

A thiuram, manzeb, or propineb pesticide standard solution (80 µg/mL in terms of carbon disulfide) was directly added to each specimen so that each concentration (in terms of carbon disulfide) was 10 ppm.

(2) Microwave-Assisted Solvent Extraction (a) Microwave-Assisted Solvent Extraction System (Hereinafter, Abbreviated as MW System)

ETHOS1 Microwave Digestion Labstation (Milestone Inc.) for microwave-assisted solvent extraction MW system main unit ETHOS1 (specification)
  Control terminal 640
  Step-up transformer MDM-1000-240-4K
  Internal temperature control kit ATC-FO
  Infrared external temperature control kit IRT
  Magnetic stirrer ASM-400
  Medium pressure segment rotor MPR-600/12 (specification)
    Bottom plate
    Top plate
    Medium pressure segment for MPR-600/12
    Spring HTC-600
    Adapter plate AP-45/HT
    TFM cover SD-05/S
    Indicator ring IR-54/25
    TFM digestion vessel (100 mL) HPV-100
    Protection shield SS-05
    Medium pressure segment for ATC
    ATC cover set (with no pressure port)
  Others
    ATC ceramic thermowell 140 mm ATC-FO (yellow cover AN0532)
    TFM rotor ($\phi$8 mm×20 mm)
    Torque wrench (22.5 Nm)

(b) Extraction Using MW System

A ground crude drug specimen (2.0 g) was weighed and added to each Teflon vessel (100 mL) and then the vessel was embedded in a protection shield. A stirrer was placed within each digestion vessel and then 10 mL of isooctane and 30 mL of a catalyst solution were immediately added thereto. The vessel was closed with a TFM cover. An adapter plate, a spring, and a protection ring were embedded, and then the vessel was installed in a medium pressure segment, followed by tightening with a torque wrench (22.5 Nm). Similar operations were carried out for the number of vessels to be subjected to measurement. The bottom plate of a segmented medium pressure rotor was set in advance within an ETHOS1 oven, so that medium pressure segments were installed to symmetrically to each other with respect to a point, and then the top plate was fitted to the top. Separately, for an internal temperature sensor, an ATC cover set was attached to a TFM vessel to which a TFM rotor, 10 mL of isooctane, and 30 mL of a catalyst solution had been added, followed by installation in a medium pressure segment for ATC, and then tightening with a torque wrench (22.5 Nm). A temperature sensor probe was inserted into a thermowell of a medium pressure segment for ATC and a connector within the ETHOS 1 oven, so as to install the medium pressure segment for ATC on the bottom plate. The door of ETHOS1 was closed and then a microwave-assisted extraction program was initiated under the conditions described in Table 1 below. After the program was completed, it was confirmed that the reaction vessels had been sufficiently cooled. The upper layer (isooctane) of each reaction solution was collected in a sample vial, so that a GC analytical sample was prepared.

TABLE 1

Example: Crude drug
4% Aqueous L-cysteine solution test
Microwave conditions

| | time/minute | Microwave Power Upper limit/W | Temperature/° C. | Stirrer Power/% |
|---|---|---|---|---|
| $1^{st}$ step | 5 | 1200 | Room temperature→100 | 80 |
| $2^{nd}$ step | 25 | 600 | 100 | 80 |
| $3^{rd}$ step | 100 | 0 | 100→Room temperature | 80 |

(c) Preparation of Carbon Disulfide Solutions for a Calibration Curve

Isooctane was added in a volume of about half of 25 ml to a 25-mL brown measuring flask, the flask was stoppered, and then the mass of the measuring flask was measured accurately. One mL of carbon disulfide was accurately weighed and added to the flask, the flask was stoppered, and then the mass of the measuring flask was measured accurately. The solution was accurately diluted with isooctane to 25 mL, so as to prepare a stock solution A (approximately 50,000 µg/mL).

The stock solution A (1 mL) was accurately weighed and then the solution was accurately diluted with isooctane to 50 mL, so as to prepare a stock solution B (approximately 1,000 µg/mL).

The stock solution B (1 mL) was accurately weighed and then accurately diluted with isooctane to 50 mL, so as to prepare a stock solution C (approximately 20 µg/mL).

The stock solution C (5 mL) was accurately weighed and then accurately diluted with isooctane to 25 mL, so as to prepare a standard solution 1 (equivalent to 4.0 µg/mL).

The standard solution 1 (10 mL) was accurately weighed and then accurately diluted with isooctane to 20 mL, so as to prepare a standard solution 2 (equivalent to 2.0 µg/mL).

The standard solution 2 (10 mL) was accurately weighed and then accurately diluted with isooctane to 20 mL, so as to prepare a standard solution 3 (equivalent to 1.0 mg/mL).

The standard solution 3 (10 mL) was accurately weighed and then accurately diluted with isooctane to 20 mL, so as to prepare a standard solution 4 (equivalent to 0.5 µg/mL).

The standard solution 4 (10 mL) was accurately weighed and then accurately diluted with isooctane to 25 mL, so as to prepare a standard solution 5 (equivalent to 0.2 µg/mL).

(3) Analytical Procedures Using a Gas Chromatograph (a) Gas Chromatography system System Identification No.: GC-7 (GC-FPD/FPD)
  6890N (Agilent Technologies, main body)
  7683 (Agilent Technologies, autosampler)
  Inlets: split/splitless inlet
  Inserts: split/splitless liner (Agilent Technologies, 5183-4711)
  Detector: FPD detector (Agilent Technologies, sulfur mode wavelength filter, 393 nm)

(b) GC-FPD Analysis Conditions
  Column: GS-GasPro (Agilent Technologies, length: 15 m, inner diameter: 0.32 mm, and membrane pressure: 0)
  Column temperature: 40° C. (1.5 min)→30° C./min→220° C. (6.5 min)
  Inlet temperature: 120° C.
  Injection mode and amount injected:split (10:1), 1 µL
  Carrier gas: helium, constant flow mode, average linear velocity 37 cm/sec
  Detector: FPD-S (temperature: 220° C., hydrogen flow rate: 50 mL/min, air flow rate: 60 mL/min, and nitrogen+helium flow rate: 50 mL/min)

(c) Preparation of a Calibration Curve

The carbon disulfide standard solutions 1-5 for a calibration curve were each analyzed once by GC-FPD. Linear regression was carried out by a least square method based on the common logarithm (Yi) of peak area value (Y) with respect to the common logarithm (Xi) of carbon disulfide concentration (X), so that a calibration curve was prepared.

(iv) Calculation of Concentrations in Analytical Samples and Handling of Numerical Values The common logarithm (yi) of peak area (y) of carbon disulfide was found. Pesticide concentration (X ppm in terms of carbon disulfide) was calculated by the following calculation method using slope "a" and yi intercept "b" in primary formula Yi=aXi+b of the calibration curve.

$$X(\text{ppm}) = 10^{(yi-b)/a} \times C$$

(correction coefficient=C: ratio of the amount of isooctane added to 1 g of a specimen)

Recovery percentage was found by calculating the concentration of a pesticide in an analytical sample as a percentage relative to the accurate concentration (in terms of carbon disulfide) in a pesticide standard solution added. Upon measurement with N=1, recovery figures were rounded off to the first decimal place. Upon measurement with N=3, recovery figures were truncated to two decimal places, and then average or relative standard deviation (RSD) was rounded off to the first decimal place.

(4) Test Results and Discussion

As shown in Table 2, it was confirmed in all the 20 kinds of crude drugs that the results of the addition and recovery test for the 3 kinds of pesticides satisfied the recovery percentages ranging from 70% to 120%, which is a requirement for successful analytical tests for residual pesticides.

TABLE 2

Crude drug Microwave-assisted method
Addition and recovery test
(Cysteine method . . . 4.0% cysteine solution)
Standard (3 pesticides) Recovery 70-120%
Relative standard deviation 10≧

| | | Crude drug name | | | |
|---|---|---|---|---|---|
| | | Japanese Angelica Root | *Cnidium* Rhizome | Moutan Bark | Bitter Orange Peel (Tohi) |
| | | | Measuring instrument | | |
| | | FPD | FPD | FPD | FPD |
| | | | | Index | |
| | Pesticide name | Average value | Average value | Average value | Average value |
| EB | Manzeb | 77.3 | 76.4 | 80.4 | 85.4 |
| DD | Thiuram | 112.0 | 99.5 | 100.1 | 91.8 |
| PB | Propineb | 77.2 | 71.7 | 70.1 | 74.9 |

| | | Crude drug name | | | |
|---|---|---|---|---|---|
| | | *Citrus Unshiu* Peel | *Pinellia* Tuber | *Bupleurum* Root | *Asiasarum* Root |
| | | | Measuring instrument | | |
| | | FPD | FPD | FPD | FPD |
| | | | | Index | |
| | Pesticide name | Average value | Average value | Average value | Average value |
| EB | Manzeb | 87.5 | 82.1 | 73.8 | 80.7 |
| DD | Thiuram | 115.0 | 107.6 | 91.1 | 101.3 |
| PB | Propineb | 78.7 | 79.4 | 73.2 | 70.9 |

| | | Crude drug name | | | |
|---|---|---|---|---|---|
| | | *Dioscorea* Rhizome | *Polygala* Root | Jujube | Immature Orange |
| | | | Measuring instrument | | |
| | | FPD | FPD | FPD | FPD |
| | | | | Index | |
| | Pesticide name | Average value | Average value | Average value | Average value |
| EB | Manzeb | 91.1 | 74.2 | 73.0 | 82.0 |
| DD | Thiuram | 111.2 | 92.1 | 110.5 | 100.6 |
| PB | Propineb | 83.3 | 81.5 | 77.2 | 76.4 |

TABLE 2-continued

| | | Crude drug Microwave-assisted method Addition and recovery test (Cysteine method . . . 4.0% cysteine solution) | Standard (3 pesticides) Recovery 70-120% | | Relative standard deviation 10≧ |
|---|---|---|---|---|---|
| | | Crude drug name | | | |
| | | Schisandra Fruit | Achyranthes Root | Ophiopogon Tuber | Angelica Dahurica Root |
| | | | Measuring instrument | | |
| | | FPD | FPD | FPD | FPD |
| | | | Index | | |
| | Pesticide name | Average value | Average value | Average value | Average value |
| EB | Manzeb | 79.0 | 71.7 | 77.7 | 72.6 |
| DD | Thiuram | 107.2 | 90.6 | 91.9 | 107.5 |
| PB | Propineb | 77.2 | 73.4 | 73.9 | 71.5 |
| | | Crude drug name | | | |
| | | Perilla Herb | Zanthoxylum Fruit | Common Wheat Seed | Loquat Leaf |
| | | | Measuring instrument | | |
| | | FPD | FPD | FPD | FPD |
| | | | Index | | |
| | Pesticide name | Average value | Average value | Average value | Average value |
| EB | Manzeb | 81.7 | 82.2 | 81.7 | 71.4 |
| DD | Thiuram | 97.9 | 86.0 | 97.9 | 96.2 |
| PB | Propineb | 74.9 | 70.8 | 74.9 | 78.6 |

Example 2

Addition and Recovery Test for Manzeb in Crude Drugs Using a 4.0% Aqueous L-Cysteine Solution as a Catalyst Test Solution (1) Specimens, Reagents, and Others
(a) Specimens The following 80 kinds of crude drugs were used as specimens in their original forms or used as specimens after they had been cut, ground, or the like to portions about 3 mm to 5 mm each.

Peony Root, Cinnamon Bark, *Poria* Sclerotium, *Cyperus* Rhizome, Peach Kernel, *Glycyrrhiza*, *Coptis* Rhizome, Ginger, Clove, *Corydalis* Tuber, *Pueraria* Root,*Glehnia* Root, *Astragalus* Root, *Scutellaria* Root, *Platycodon* Root, Rhubarb, *Sinomenium* Stem, *Saposhnikovia* Root, *Phellodendron* Bark, *Magnolia* Bark, *Mentha* Herb, *Ephedra* Herb, *Schizonepeta* Spike, Fennel, *Evodia* Fruit, *Gardenia* Fruit, *Trichosanthes* Seed, Apricot Kernel, Burdock Fruit, Jujube Seed, *Plantago* Seed, Sesame, *Benincasa* Seed, *Coix* Seed, *Magnolia* Flower, Gelatin, Cicada Periostracum, *Trichosanthes* Root, Araliae Cordata Root, *Sophora* Root Processed Ginger, *Peucedanum* Root, *Anemarrhena* Rhizome, *Gastrodia* Tuber, *Asparagus* Tuber, *Aralia* Rhizome, *Atractylodes* Rhizome, *Saussurea* Root, *Cimicifuga* Rhizome, Japanese Valerian (Kissokon), *Clematis* Root, *Senna* Leaf (*Senna*), *Artemisia Capillaris*Flower, *Artemisia* Leaf, *Uncaria* Hook, *Lycium* Bark, *Quercus* Bark, *Cornus* Fruit, Hemp, *Forsythia* Fruit, Longan Aril *Polyporus* Sclerotium, *Areca*, Malt, *Amomum* Seed, Brown Rice, *Akebia* Stem, *Chrysanthemum* Flower, *Alpinia Officinerum* Rhizome, *Nelumbo* Seed, Safflower, *Loniccra* Leaf and Stem, *Tribulus* Fruit, *Polygonum* Root, Bamboo Trunk, *Nuphar* Rhizome, Mulberry Bark, *Arisaema* Tuber, Sappan Wood, *Fritillaria* Bulb, *Notopterigum* , *Lilium* Bulb, *Lithospermum* Root, Processed Aconite Root, *Eucommia* Bark, *Crataegus* Fruit, Prepared *Rehmannia* Root (Jukujio), Ipecac (Tokon), Maltose, and *Panax Japonicus* Rhizome (Chikusetsuninjin).

(1) An addition and recovery test was conducted under the same conditions as those in Example 1, except that (a) specimens and manzeb as a target pesticide of the addition and recovery test were used.

(4) Test Results and Discussion

As shown in Table 3, it was confirmed in all the 80 kinds of crude drugs that the results of the addition and recovery test for manzeb satisfied recovery percentages ranging from 70% to 120%, which is a requirement for successful analytical test for residual pesticides.

TABLE 3

Crude drug Microwave-assisted method Addition and recovery test
(Other than 27 N = 1, Manzeb. 4.0% cysteine solution)

| | Crude drug name | | | | | | | |
|---|---|---|---|---|---|---|---|---|
| | Peony Root | Cinnamon Bark | *Poria Sclerotium* | *Cyperus* Rhizome | Peach Kernel | *Glycyrrhiza* | *Coplis* Rhizome | Ginger | Clove | *Corydalis* Tuber |
| Manzeb recovery | 84.8 | 89.9 | 89.2 | 80.5 | 75.9 | 82.6 | 75.4 | 78.5 | 85.8 | 82.7 |

| | Crude drug name | | | | | | | |
|---|---|---|---|---|---|---|---|---|
| | *Pueraria* Root | *Glehnia* Root | *Astragalus* Root | *Scutellaria* Root | *Platycodon* Root | Rhubarb | *Sinomenium* Stem | *Saposhnikovia* Root | *Phellodendron* Bark |
| Manzeb recovery | 81.2 | 80.3 | 82.4 | 76.9 | 81.9 | 86.3 | 75.7 | 79.4 | 80.2 |

| | Crude drug name | | | | | | | |
|---|---|---|---|---|---|---|---|---|
| | *Mentha* Herb | *Ephedra* Herb | *Schizonepeta* Spike | Fennel Fruit | *Evodia* Fruit | *Gardenia* Fruit | *Trichosanthes* Seed | Apricot Kernel | Jujube Seed |
| Manzeb recovery | 77.5 | 90.8 | 78.1 | 83.8 | 84.6 | 77.2 | 77.1 | 74.8 | 85.0 |

| | Crude drug name | | | | | | | |
|---|---|---|---|---|---|---|---|---|
| | *Plantago* Seed | *Benincasa* Seed | Sesame | Coix Seed | *Magnolia* Flower | Gelatin | *Cicada* Periostracum | *Trichosanthes* Root | *Araliae Cordata* Root |
| Manzeb recovery | 71.3 | 81.9 | 76.4 | 75.2 | 77.1 | 88.3 | 74.0 | 82.4 | 82.2 |

| | Crude drug name | | | | | | | |
|---|---|---|---|---|---|---|---|---|
| | Processed Ginger | *Peucedanum* Root | *Anemarrhena* Rhizome | *Gastrodia* Tuber | Chinese Asparagus Tuber | *Aralia* Rhizome | *Atractylodes* Rhizome | *Saussurea* Root | *Cimicifuga* Rhizome | Japanese Vaterian (Kissokon) |
| Manzeb recovery | 77.6 | 72.4 | 79.3 | 86.8 | 89.5 | 84.6 | 77.8 | 72.3 | 82.6 | 83.5 |

| | Crude drug name | | | | | | | |
|---|---|---|---|---|---|---|---|---|
| | *Clematis* Root | Senna Leaf (Senna) | *Artemisia* Capillaris | *Artemisia* Leaf | *Uncaria* Hook | *Lycium* Bark | Oak Bark | *Cornus* Fruit | Hemp | *Forsythia* Fruit |
| Manzeb recovery | 75.1 | 80.0 | 87.4 | 91.3 | 97.7 | 92.8 | 99.9 | 90.4 | 95.2 | 88.2 |

TABLE 3-continued

Crude drug Microwave-assisted method Addition and recovery test
(Other than 27 N = 1, Manzeb. 4.0% cysteine solution)

| | Crude drug name | | | | | | | |
|---|---|---|---|---|---|---|---|---|
| | Longan Fruit | Polyporus Sclerotium | Areca | Malt | Amomum Seed | Brown Rice | Akebie Stem | Chrysanthemum Flower | Alpinia Officinarum Rhizome | Nelumbo Seed |
| Manzeb recovery | 92.7 | 101.1 | 92.3 | 91.9 | 87.5 | 85.5 | 81.8 | 81.8 | 84.5 | 83.1 |

| | Crude drug name | | | | | | | |
|---|---|---|---|---|---|---|---|---|
| | Safflower | Lonicera Leaf and Stem | Tribulus Fruit | Polygonum Root | Bamboo Trunk | Naphar Rhizome | Mulberry Bark | Arisaema Tuber | Sappan Wood | Fritillaria Bulb |
| Manzeb recovery | 72.0 | 77.8 | 78.9 | 85.0 | 77.3 | 94.8 | 90.1 | 82.9 | 82.8 | 87.2 |

| | Crude drug name | | | | | | |
|---|---|---|---|---|---|---|---|
| | Notopterigum Rhizome | Lilium Bulb | Lithospermum Root | Processed Aconite Root | Eucommia Bark | Crataegus Fruit | Prepared Rehmannia Root (Jukujio) | Ipecac (Tokon) | Maltose | Panax Japonicus Rhizome (Chikusetsuninjin) |
| Manzeb recovery | 73.4 | 88.6 | 74.7 | 75.6 | 88.9 | 77.5 | 77.1 | 82.0 | 96.0 | 73.2 |

Measuring instrument: FPD

Example 3

Addition and Recovery Test for Thiuram Manzeb and Propineb in Crude Drugs Using 5 Mol/L Hydrochloric Acid Containing 1.5% Tin Chloride and 1% L-Cysteine as a Catalyst Test Solution (1) Specimens, Reagents, and Others (a) Specimens The following 5 kinds of crude drugs were used as specimens in their original forms or used as specimens after they had been cut, ground, or the like to portions about 3 mm to 5 mm each.

*Atractylodes* Lancea Rhizome, *Alisma* Rhizome, *Rehmannia* Root, Ginseng, and Japanese Gentian (b) Reagents-Test Solutions Hydrochloric acid: Wako Pure Chemical Industries, Ltd., special grade reagent Tin (II) chloride dihydrate: Kanto Chemical Co., Inc., special grade reagent, reagent purity 97.0%, JIS K8136

L-cysteine hydrochloride monohydrate: Wako Pure Chemical Industries, Ltd., special grade reagent, reagent purity 99.0%

Cyclohexane: Kanto Chemical Co., Inc., for testing residual pesticides 2,2,4-trimethylpentane (isooctane): Kanto Chemical Co., Inc., Extra pure Acetone: Kanto Chemical Co., Inc., for testing residual pesticides Distilled water (washed with hexane): Wako Pure Chemical Industries, Ltd., for testing residual pesticides 5.0 mol/L hydrochloric acid solution: Purified water was slowly added to 1240 mL of hydrochloric acid, so as to prepare 3000 mL of the 5.0 mol/L hydrochloric acid solution.

(c) Catalyst Test Solution 1.5% tin chloride 5.0 mol/L hydrochloric acid solution: Tin (II) chloride dihydrate (9.20 g) was accurately weighed and then 5.0 mol/L hydrochloric acid was added, so as to prepare 500 mL of the solution.

1% L-cysteine 1.5% tin chloride 5.0 mol/L hydrochloric acid solution: Tin (II) chloride dihydrate (9.2 g) was weighed, 7.3 g of L-cysteine hydrochloride monohydrate was weighed, and then 5.0 mol/L hydrochloric acid was added, so as to prepare 500 mL of the 1% L-cysteine 1.5% tin chloride 5.0 mol/L hydrochloric acid solution.

(d) Pesticides to be tested and (e) pesticides added were the same as those in Example 1.

(2) Microwave-Assisted Solvent Extraction (a) MW System was the Same as in Example 1.

(b) Extraction Using MW System

A ground crude drug specimen (2.0 g) was weighed and added to each Teflon vessel (100 mL) and then the vessel was embedded in a protection shield. A stirrer was placed within each digestion vessel and then 10 mL of isooctane and 30 mL of a catalyst solution were immediately added thereto. The vessel was closed with a TFM cover. An adapter plate, a spring, and a protection ring were embedded, and then the vessel was installed in a medium pressure segment, followed by tightening with a torque wrench (22.5 Nm). Similar operations were carried out for the number of vessels to be subjected to measurement. The bottom plate of a segmented medium pressure rotor was set in advance within an ETHOS1 oven, so that medium pressure segments were installed to symmetrically to each other with respect to a point, and then the top plate was fitted to the top. Separately, for an internal temperature sensor, an ATC cover set was attached to a TFM vessel to which a TFM rotor, 10 mL of isooctane, and 30 mL of a catalyst solution had been added, followed by installation in a medium pressure segment for ATC, and then tightening with a torque wrench (22.5 Nm). A temperature sensor probe was inserted into a thermowell of a medium pressure segment for ATC and a connector within the ETHOS1 oven, so as to install the medium pressure segment for ATC on the bottom plate. The door of ETHOS1 was closed and then a microwave-assisted extraction program was initiated under the conditions described in Table 4 below. After the program was completed, it was confirmed that the reaction vessels had been sufficiently cooled. The upper layer (isooctane) of each reaction solution was collected in a sample vial, so that a GC analytical sample was prepared.

TABLE 4

Example: Crude drug
Tin chloride test
Microwave conditions

| | Microwave time/minute | Power Upper limit/W | Temperature/° C. | Stirrer Power/% |
|---|---|---|---|---|
| 1$^{st}$ step | 7 | 1200 | Room temperature→90 | 80 |
| 2$^{nd}$ step | 23 | 800 | 90 | 80 |
| 3$^{rd}$ step | 100 | 0 | 90→Room temperature | 80 |

(c) Preparation of Carbon Disulfide Solutions for a Calibration Curve

Same as Example 1.

(3) Analytical Procedures Using a Gas Chromatograph

Same as Example 1.

(4) Test Results and Discussion

As shown in Table 5, it was confirmed in the 5 kinds of crude drugs that the results of the addition and recovery test for 3 kinds of pesticides (other than propineb in *Atractylodes Lancea* Rhizome) satisfied recovery percentages ranging from 70% to 120%, which is a requirement for successful analytical tests for residual pesticides.

TABLE 5

Crude drug Microwave-assisted method
Addition and recovery test
(Tin-hydrochloric acid method ... 1% tin - 1.5% cysteine - 5 mol/L hydrochloric acid)

Standard (3 pesticides) Recovery 70-120%

Relative standard deviation 10≧

Crude drug name

|  |  | Atractylodes Lancea Rhizome | Alisma rhizome | Rehmannia Root (dried) | Ginseng | Japanese Gentian |
|---|---|---|---|---|---|---|
|  |  | Measuring instrument | | | | |
|  |  | FPD | FPD | FPD Index | FPD | FPD |
| Pesticide name | | Average value | Average value | Average value | Average value | Average value |
| EB | Manzeb | 75.3 | 75.4 | 75.6 | 83.5 | 80.0 |
| DD | Thiuram | 80.7 | 91.8 | 95.6 | 93.8 | 94.0 |
| PB | Propineb | 63.1 | 82.8 | 80.9 | 75.2 | 72.0 |

Example 4

Addition and Recovery Test for Thiuram in Crude Drugs Using 1.0% Aqueous L-Cysteine Hydrochloride Solution as a Catalyst Test Solution (1) Specimens, Reagents, and Others
(a) Specimens Immature Orange, *Cnidium* Rhizome, and *Zanthoxylum* Fruit were used as specimens in their original forms or used as specimens after they had been cut, ground, or the like to portions about 3 mm to 5 mm each.
(b) Reagents Test Solutions
L-cysteine hydrochloride monohydrate: Wako Pure Chemical Industries, Ltd., special grade reagent
2,2,4-trimethylpentane (isooctane): Kanto Chemical Co., Inc., extra pure
Aacetone: Kanto Chemical Co., Inc., for testing residual pesticides
Distilled water (washed with hexane): Wako Pure Chemical Industries, Ltd., for testing residual pesticides
(c) Catalyst Test Solution
1.0% aqueous cysteine solution: L-cysteine hydrochloride monohydrate (5.0 g) was dissolved in distilled water, so as to prepare 500 mL of the solution.
(d) Pesticide Tested
Pesticide Reference Standard
Carbon disulfide: Wako Pure Chemical Industries, Ltd., special grade reagent, and reagent purity 99%
Thiuram reference standard: Wako Pure Chemical Industries, Ltd., pesticide reference standard, and reagent purity 100%
Preparation of a Pesticide Standard Solution
A thiuram standard solution (80 μg/mL (in terms of carbon disulfide) solution): Thiuram (3.16 mg) was weighed and then acetone was added thereto, so as to prepare accurately 25 mL of the thiuram standard solution.
(e) Pesticides Added
Thiuram pesticide standard solution (80 μg/mL in terms of carbon disulfide) was directly added to each specimen using a micropipette, so that the concentration (in terms of carbon disulfide) was 10 ppm.

(2) Microwave-Assisted Solvent Extraction
The test system, test conditions, and the like are basically the same as those in Example 1. Table 6 shows conditions for the microwave assisted extraction program.

TABLE 6

Example: Thiuram test
Microwave conditions

| | time/ minute | Microwave Power Upper limit/W | Temperature/° C. | Stirrer Power/% |
|---|---|---|---|---|
| 1$^{st}$ step | 7 | 1500 | Room temperature→90 | 80 |
| 2$^{nd}$ step | 10 | 1000 | 90 | 80 |
| 3$^{rd}$ step | 100 | 0 | 90→Room temperature | 80 |

(3) Analytical Procedures Using a Gas Chromatograph
Same as Example 1.
(4) Test Results and Discussion
As shown in Table 7, it was confirmed in the 5 kinds of crude drugs that the results of the addition and recovery test for 3 kinds of pesticides (other than propineb in *Atractylodes Lancea* Rhizome) satisfied recovery percentages ranging from 70% to 120%, which is a requirement for successful analytical tests for residual pesticides.

TABLE 7

Thiuram addition and recovery test results

| Crude drug name | Recovery (%) | RSD (%) |
|---|---|---|
| Immature Orange | 100.2 | 0.5 |
| *Cnidium* Rhizome | 92.0 | 1.8 |
| *Zanthoxylum* Fruit | 88.2 | 3.1 |

Example 5

Addition and Recovery Test for Manzeb Using 0.5%, 1.0%, and 2.0% Aqueous L-Cysteine Solutions as Catalyst Test Solutions (1) Specimens, Reagents, and Others
(a) Specimens Immature Orange, *Cnidium* Rhizome, *Zanthoxylum* Fruit, and *Perilla* Herb were used as specimens in their original forms or used as specimens after they had been cut, ground; or the like to portions about 3 mm to 5 mm each.

(b) Reagents Test Solutions

L-cysteine hydrochloride monohydrate: Wako Pure Chemical Industries, Ltd., special grade reagent 2,2,4-trimethylpentane (isooctane): Kanto Chemical Co., Inc., Extra pure Acetone: Kanto Chemical Co., Inc., for testing residual pesticides Distilled water (washed with hexane): Wako Pure Chemical Industries, Ltd., for testing residual pesticides (c) Catalyst Test Solutions 0.5% aqueous cysteine solution: L-cysteine hydrochloride monohydrate (2.5 g) was dissolved in distilled water, so as to prepare 500 mL of the solution.

1.0% aqueous cysteine solution: L-cysteine hydrochloride monohydrate (5.0 g) was dissolved in distilled water, so as to prepare 500 mL of the solution.

2.0% aqueous cysteine solution: L-cysteine hydrochloride monohydrate (10.0 g) was dissolved in distilled water, so as to prepare 500 mL of the solution.

(d) Pesticides Tested

Pesticide Reference Standard

Carbon disulfide: Wako Pure Chemical Industries, Ltd., special grade reagent, and reagent purity 99%

Manzeb reference standard: Wako Pure Chemical Industries, Ltd., pesticide reference standard, and reagent purity 91%

Preparation of a Pesticide Standard Solution

Manzeb standard solution (80 µg/mL (in terms of carbon disulfide) solution): Manzeb (3.89 mg) was weighed, distilled water or acetonitrile was added, and then ultrasonic irradiation was carried out to prepare a suspended solution. Thus, accurately 25 mL of the manzeb standard solution was prepared.

(e) Pesticides Added

A manzeb pesticide standard solution (80 µg/mL in terms of carbon disulfide) was directly added to each specimen using a micropipette, so that the concentration (in terms of carbon disulfide) was 10 ppm.

(2) Microwave-Assisted Solvent Extraction

The test system, test conditions, and the like are basically the same as those in Example 1. Table 8 shows conditions for the microwave-assisted extraction program.

TABLE 8

| | time/ minute | Microwave Power Upper limit/W | Temperature/° C. | Stirrer Power/% |
|---|---|---|---|---|
| Manzeb test Microwave conditions (L-cysteine 0.5%, 1.0%) | | | | |
| 1$^{st}$ step | 7 | 1500 | Room temperature→90 | 80 |
| 2$^{nd}$ step | 10 | 1000 | 90 | 80 |
| 3$^{rd}$ step | 100 | 0 | 90→Room temperature | 80 |
| Manzeb test Microwave conditions (L-cysteine 2.0%) | | | | |
| 1$^{st}$ step | 7 | 1200 | Room temperature→100 | 80 |
| 2$^{nd}$ step | 23 | 800 | 100 | 80 |
| 3$^{rd}$ step | 100 | 0 | 100→Room temperature | 80 |

(3) Analytical Procedures Using a Gas Chromatograph
  Same as Example 1

(4) Test Results and Discussion

As shown in Table 9, it was confirmed that the results of the addition and recovery test for manzeb using 4 kinds of crude drugs did not satisfy the recovery percentage requirements ranging from 70% to 120% when the catalyst test solution was 0.5% or 1.0% aqueous L-cysteine solution, but the results for all 4 kinds of crude drugs satisfied the same when the catalyst test solution was 2.0% aqueous L-cysteine solution.

TABLE 9

Manzeb addition and recovery test results

| Crude drug name | Catalytic reagent | Recovery (%) |
|---|---|---|
| Immature Orange | 0.5% Aqueous L-cysteine solution | 51.2 |
| Cnidium Rhizome | " | 33.6 |
| Zanthoxylum Fruit | " | 50.6 |
| Perilla Herb | " | 55.7 |
| Immature Orange | 1.0% Aqueous L-cysteine solution | 54.1 |
| Cnidium Rhizome | " | 44.9 |
| Zanthoxylum Fruit | " | 65.1 |
| Perilla Herb | " | 54.4 |
| Immature Orange | 2.0% Aqueous L-cysteine solution | 86.4 |
| Cnidium Rhizome | " | 73.2 |
| Zanthoxylum Fruit | " | 91.4 |
| Perilla Herb | " | 93.6 |

Example 6

Reagents test solutions, reference standards, and methods for preparing pesticide standard solutions employed in Example 6 are as follows.

1: Reagents Test Solutions

Hydrochloric acid: Wako Pure Chemical Industries, Ltd., special grade reagent

Tin (II) chloride dihydrate: Kanto Chemical Co., Inc., special grade reagent, reagent purity 97.0%, JIS K8136

L-cysteine hydrochloride monohydrate: Wako Pure Chemical Industries, Ltd., special grade reagent, reagent purity 99.0%

Cyclohexane: Kanto Chemical Co., Inc., for testing residual pesticides 2,2,4-trimethylpentane (isooctane): Kanto Chemical Co., Inc., extra pure Acetone: Kanto Chemical Co., Inc., for testing residual pesticides Distilled water (washed with hexane): Wako Pure Chemical Industries, Ltd., for testing residual pesticides 5.0 mol/L hydrochloric acid solution: Purified water was slowly added to 1240 mL of hydrochloric acid, so as to prepare 3000 mL of the solution.

1.5% tin chloride 5.0 mol/L hydrochloric acid solution: Tin (II) chloride dihydrate (9.20 g) was accurately weighed and then 5.0 mol/L hydrochloric acid was added, so as to prepare 500 mL of the solution.

1% L-cysteine 1.5% tin chloride 5.0 mol/L hydrochloric acid solution: Tin (II) chloride dihydrate (9.2 g) was weighed, 7.3 g of L-cysteine hydrochloride monohydrate was weighed, and then 5.0 mol/L hydrochloric acid was added, so as to prepare 500 mL of the solution.

2. Reference Standards and Preparation of Pesticide Standard Solutions

Carbon disulfide: Wako Pure Chemical Industries, Ltd., special grade reagent, JIS K8732

Thiuram reference standard: Wako Pure Chemical Industries, Ltd., pesticide reference standard, reagent purity 100%

Propineb reference standard: GL Sciences Inc., pesticide reference standard, reagent purity 80% or more Thiuram standard solution (20 µg/mL (in terms of carbon disulfide) solution): Thiuram (3.16 mg) was weighed and then acetone was added thereto, so as to accurately prepare 100 mL of the solution.

Propineb standard solution (20 µg/mL (in terms of carbon disulfide) solution): Propineb (4.75 mg) was weighed, distilled water was added, and then ultrasonic fragmentation and suspension were carried out, so as to accurately prepare 100 mL of the solution.

A. Pretreatment

System (Microwave-Assisted Solvent Extractor):

ETHOS1 (MILESTONE, microwave oven body, option: internal temperature sensor and magnetic stirrer)

PRO24 (MILESTONE, rotor for simultaneous treatment of 24 vessels)

Stirrer (diameter 6 mm×full length 20 mm)

Procedures for Pretreatment:

A Teflon vessel (reaction cylindrical vessel, 70 mL) was directly placed on a scale, a specimen was accurately weighed, and then a stirrer was placed therein. Isooctane or cyclohexane (5.0 mL) was added to the vessel using a dispenser pipette. In the case of an addition and recovery test, a pesticide standard solution was then added thereto using a dispenser pipette. Thirty (30) mL of an L-cysteine, tin (II) chloride dihydrate 5.0 mol/L hydrochloric acid solution was added to the solution using a dispenser. After being closed with a Teflon cover, the vessel was placed in a pressure container, and then a safety valve was closed. Similar procedures were carried out for the number of vessels to be subjected to measurement. A single pressure container was assembled, in which an internal temperature sensor had been separately installed. The pressure containers were arranged in a circularly symmetrical manner with respect to the rotor body and then covered. An internal temperature sensor probe was then attached, and then the pressure containers were positioned in the oven body. Then, the pretreatment method described in the Results was carried out.

After completion of the pretreatment method, pressure containers were removed and then the safety valves were opened. Each Teflon vessel was removed, the Teflon cover was removed, and then the organic layer was sampled in a vial for measurement using a Pasteur pipette.

A temperature sensor was installed to one of the reaction vessels. Each reaction vessel was arranged so that the positions thereof were evenly distributed to be symmetrical with respect to a certain point and then the treatment method was carried out.

B. Preparation of Carbon Disulfide Solutions for a Calibration Curve

Cyclohexane was added in a volume of about half of 25 ml to a 25-mL brown measuring flask, the flask was stoppered, and then the mass of the measuring flask was measured accurately. One mL of carbon disulfide was accurately weighed and added to the flask, the flask was stoppered, and then the mass of the measuring flask was measured accurately. The solution was accurately diluted with cyclohexane to 25 mL, so as to prepare a standard stock solution.

One (1) mL of the standard stock solution was accurately weighed and then accurately diluted with cyclohexane to 50 mL, so as to prepare a 1000 µg/mL, solution.

One (1) mL of the 1000 µg/mL solution was accurately weighed and then accurately diluted with cyclohexane to 50 mL, so as to prepare a 20 µg/mL solution.

One (1) mL of the 20 µg/mL solution was accurately weighed and then accurately diluted with cyclohexane to 25 mL, so as to prepare a standard solution 1 (0.8 µg/mL).

Ten (10) mL of the standard solution 0.1 was accurately weighed and then accurately diluted with cyclohexane to 20 mL, so as to prepare a standard solution 2 (0.4 µg/mL).

Ten (10) mL of the standard solution 2 was accurately weighed and then accurately diluted with cyclohexane to 20 mL, so as to prepare a standard solution 3 (0.2 µg/mL).

Ten (10) mL of the standard solution 3 was accurately weighed and then accurately diluted with cyclohexane to 20 mL, so as to prepare a standard solution 4 (0.1 µg/mL).

Ten (10) mL of the standard solution 4 was accurately weighed and then accurately diluted with cyclohexane to 25 mL, so as to prepare a standard solution 5 (0.04 µg/mL).

C. Results and Discussion

1. Examination of Analysis Conditions and the Calibration Curve

GS-GasPro was used as an analytical column since contaminant peaks and carbon disulfide peaks appear significantly distant from each other and sufficient separation can be achieved with a general carrier gas flow rate.

(1) GS-FPD Conditions for the Use of GS-GasPro

Apparatus (Gas Chromatograph)

6890N (Agilent Technologies, main body)

7683 (Agilent Technologies, autosampler)

Inlets: split/splitless inlet, pulsed splitless mode (pulse pressure: 30 psi)

Inserts: split/splitless liner (Agilent Technologies, 5183-4711)

GC-FPD measurement conditions:

Column: GS-GasPro (Agilent Technologies, length: 15 m, inner diameter: 0.32 mm, and membrane pressure: 0)

Column temperature: 40° C. (1.5 min)→30° C./min→220° C. (1.5 min)

Inlets: split/splitless

Inlet temperature: 120° C.

Injection mode and injection amount: pulsed splitless (30 psi, 1.5 min), 1 µL

Carrier gas: helium, constant flow mode, average linear velocity 37 cm/sec

Detector: FPD-S (temperature: 220° C., hydrogen flow rate: 50 mL/min, air flow rate: 60 mL/min, and nitrogen+ helium flow rate: 50 mL/min)

(2) Preparation of a Calibration Curve

Carbon disulfide solutions for a calibration curve were analyzed under GC-FPD measurement conditions 1. A calibration curve was prepared based on the concentrations of carbon disulfide and the peak area values, and then correlation coefficients and the trueness of the concentrations of the standard solutions were found.

Calculation: Common logarithms of the peak area values were plotted (double logarithmic plotting) against common logarithms of the concentration. The linear regression correlation coefficient was found to be always as good as 0.99 or more with the use of any calculation method. Trueness was as good as within ±5% at all concentrations only in the case of linear regression obtained by double logarithmic plotting (Table 10). A portion of the calibration curve ranging from 0.04 to 0.8 µg/mL corresponds to a concentration of a pesticide in a specimen ranging from 0.2 ppm to 4 ppm.

TABLE 10

| Double logarithmic plot | | Calibration curve 1 | Calibration curve 2 | Calibration curve 3 |
|---|---|---|---|---|
| Correlation coefficient | | 0.9995 | 0.9987 | 0.9996 |
| Trueness (%) | 0.04 | 103.2 | 104.9 | 99.9 |
| | 0.1 | 96.2 | 95.6 | 98.4 |
| | 0.2 | 99.1 | 96.0 | 100.9 |
| | 0.4 | 100.0 | 100.8 | 103.7 |
| | 0.8 | 101.7 | 103.0 | 97.3 |

2. Effects by Addition of L-Cysteine (Reaction Vessel Capacity)

70 mL (simultaneous pretreatment of a maximum of 24 vessels)

(Calibration Curve)

A quantitative value was calculated using the product of a GC-FPD quantitative value based on the carbon disulfide calibration curve with 5 concentrations (0.05, 0.2, 0.4, 0.6, and 1 µg/mL) and the dilution ratio of an extraction solvent to a specimen.

(Analysis Conditions)

The above measurement conditions were employed.

(Specimen)

Hochu-ekki-to (1.0 g each) was used as a specimen.

(Pesticides Added)

A pesticide standard solution (20 μg/mL (in terms of carbon disulfide) solution) (100 μL) was added to each specimen. (2.0 μg/mL: concentration in terms of carbon disulfide in each specimen)

(Conditions for Pretreatment Test Solutions)

Cyclohexane (5.0 mL) and 30 mL of a 1.5% tin chloride 5.0 mol/L hydrochloric acid solution or 30 mL of a 1% L-cysteine 1.5% tin chloride 5.0 mol/L hydrochloric acid solution were added and then 7 vessels were treated at the same time. Table 11 shows the parameters based upon which the pretreatment method was carried out.

TABLE 11

| | time/minute | Microwave Power Upper limit/W | Temperature/° C. | Stirrer Power/% |
|---|---|---|---|---|
| $1^{st}$ step | 5 | 800 | Room temperature→100 | 80 |
| $2^{nd}$ step | 12 | 500 | 100 | 80 |
| $3^{rd}$ step | 73 | 0 | 100→Room temperature | 80 |

(Results and Discussion)

Recovery percentage (N=3) when the 1% L-cysteine 1.5% tin chloride 5.0 mol/L hydrochloric acid solution had been added was higher by about 10% than the result obtained when no L-cysteine had been added (Table 12). This may be because alternative digestion of propineb was suppressed by the addition of L-cysteine so that digestion into carbon disulfide took place rapidly.

Generally, recovery percentages ranging from 70% to 120%, which is a requirement for successful analytical methods for residual pesticide tests, could be obtained.

TABLE 12

| Specimen name | Pesticide | Acid catalyst solution | Recovery (%) | Average value |
|---|---|---|---|---|
| Hochu-ekki-to | Propineb | 1% Cysteine, 1.5% SnCl$_2$—HCl | 75.7 | 74.2 |
| | | 1% Cysteine, 1.5% SnCl$_2$—HCl | 70.9 | |
| | | 1% Cysteine, 1.5% SnCl$_2$—HCl | 76.1 | |
| Hochu-ekki-to | Propineb | 1.5% SnCl$_2$—HCl | 62.7 | 62.2 |
| | | 1.5% SnCl$_2$—HCl | 61.3 | |
| | | 1.5% SnCl$_2$—HCl | 62.5 | |

3. Effects of Extraction Solvent Upon Addition of L-Cysteine (Reaction Vessel Capacity)

70 mL (simultaneous pretreatment of a maximum of 24 vessels)

(Calibration Curve)

A quantitative value was calculated using the product of a GC-FPD quantitative value based on the carbon disulfide calibration curve with 5 concentrations (0.04, 0.1, 0.2, 0.4, and 0.8 μg/mL) and the dilution ratio of an extraction solvent to a specimen.

(Analysis Conditions)

The above measurement conditions were employed.

(Specimens)

Hochu-ekki-to (1.0 g each) and Dai-kenchu-to (1.0 g each) were used as specimens.

(Pesticides Added)

A thiuram or propineb pesticide standard solution (20 μg/mL (in terms of carbon disulfide) solution) (100 μL) was added to each specimen. (2.0 μg/mL: concentration in terms of carbon disulfide in each specimen)

(Conditions for Pretreatment Test Solutions)

Cyclohexane or isooctane (5.0 mL), and 30 mL of a 1% L-cysteine 1.5% tin chloride 5.0 mol/L hydrochloric acid solution were added and then 24 vessels were treated at the same time. Table 13 shows the parameters based upon which the pretreatment method was carried out.

TABLE 13

| | time/minute | Microwave Power Upper limit/W | Temperature/° C. | Stirrer Power/% |
|---|---|---|---|---|
| $1^{st}$ step | 5 | 1500 | Room temperature→100 | 80 |
| $2^{nd}$ step | 12 | 800 | 100 | 80 |
| $3^{rd}$ step | 73 | 0 | 100→Room temperature | 80 |

(Results and Discussion)

Table 14 shows the results. In cases of any prescriptions and any pesticides added, the recovery percentages were high when cyclohexane had been used as an extraction solvent.

TABLE 14

| Specimen name | Extraction solvent | Pesticide | Recovery (%) | Average value | RSD (%) |
|---|---|---|---|---|---|
| Hochu-ekki-to | Cyclohexane | Thiuram | 98.4 | 100.7 | 3.2 |
| | Cyclohexane | Thiuram | 103.0 | | |
| Hochu-ekki-to | Cyclohexane | Propineb | 83.2 | 80.9 | 3.6 |
| | Cyclohexane | Propineb | 81.8 | | |
| | Cyclohexane | Propineb | 77.6 | | |
| Dai-kenchu-to | Cyclohexane | Thiuram | 97.7 | 96.8 | 3.6 |
| | Cyclohexane | Thiuram | 99.7 | | |
| | Cyclohexane | Thiuram | 92.9 | | |
| Dai-kenchu-to | Cyclohexane | Propineb | 78.7 | 75.0 | 4.3 |
| | Cyclohexane | Propineb | 73.0 | | |
| | Cyclohexane | Propineb | 73.3 | | |

TABLE 14-continued

| Specimen name | Extraction solvent | Pesticide | Recovery (%) | Average value | RSD (%) |
|---|---|---|---|---|---|
| Hochu-ekki-to | Isooctane | Thiuram | 86.6 | 92.2 | 5.3 |
| | Isooctane | Thiuram | 95.3 | | |
| | Isooctane | Thiuram | 94.8 | | |
| Hochu-ekki-to | Isooctane | Propineb | 74.8 | 75.8 | 2.0 |
| | Isooctane | Propineb | 77.5 | | |
| | Isooctane | Propineb | 75.0 | | |
| Dai-kenchu-to | Isooctane | Thiuram | 91.8 | 87.1 | 4.8 |
| | Isooctane | Thiuram | 83.7 | | |
| | Isooctane | Thiuram | 85.8 | | |
| Dai-kenchu-to | Isooctane | Propineb | 65.9 | 66.3 | 1.5 |
| | Isooctane | Propineb | 65.7 | | |
| | Isooctane | Propineb | 67.4 | | |

4. Effects of Cysteine Concentrations

Changes in recovery percentages resulting from concentrations of cysteine added were examined for Hochu-ekki-to and Dai-kenchu-to. Addition was carried out with 5 concentrations (0%, 0.1%, 0.5%, 1%, and 5%).
(Reaction Vessel Capacity)
70 mL (simultaneous pretreatment of a maximum of 24 vessels)
(Calibration Curve)
A quantitative value was calculated using the product of a GC-FPD quantitative value based on a carbon disulfide calibration curve with 5 concentrations (0.04, 0.1, 0.2, 0.4, and 0.8 μg/mL) and the dilution ratio of an extraction solvent to a specimen.
(Analysis Conditions)
The above measurement conditions were employed.
(Specimens)
Hochu-ekki-to (1.0 g each) and Dai-kenchu-to (1.0 g each) were used as specimens.
(Pesticides Added)
A propineb pesticide standard solution (20 μg/mL (in terms of carbon disulfide) solution) (100 μl) was added to each specimen. (2.0 μg/mL: concentration in terms of carbon disulfide in each specimen)
(Conditions for Pretreatment Test Solutions)
Cyclohexane (5.0 mL) and 30 mL of a 1.5% tin chloride 5.0 mol/L hydrochloric acid solution or 30 mL of an L-cysteine 1.5% tin chloride 5.0 mol/L hydrochloric acid solution were added, and then 21 vessels were treated at the same time. In addition, an L-cysteine solution with each concentration was prepared according to the above method for preparing a 1% L-cysteine 1.5% tin chloride 5.0 mol/L hydrochloric acid solution. Table 15 shows the parameters based upon which the pretreatment method was carried out

TABLE 15

| | time/ minute | Microwave Power Upper limit/W | Temperature/° C. | Stirrer Power/% |
|---|---|---|---|---|
| $1^{st}$ step | 5 | 1500 | Room temperature→100 | 80 |
| $2^{nd}$ step | 12 | 800 | 100 | 80 |
| $3^{rd}$ step | 73 | 0 | 100→Room temperature | 80 |

(Results and Discussion)
Table 16 shows the results. In the case of addition and recovery of propineb in Hochu-ekki-to, the recovery percentage was found to improve as the concentration of L-cysteine increased.

TABLE 16

| Specimen name | Cysteine concentration | Average recovery (%) |
|---|---|---|
| Hochu-ekki-to | 0% | 66.6 |
| | 0.1% | 77.2 |
| | 0.5% | 80.0 |
| | 1% | 82.7 |
| | 5% | 88.7 |
| Dai-kenchu-to | 0% | 72.4 |
| | 0.1% | 73.4 |
| | 0.5% | 72.4 |
| | 1% | 71.2 |
| | 5% | 77.0 |

5. Effects of Pretreatment Reaction Time
(Reaction vessel capacity)
70 mL (simultaneous pretreatment of a maximum of 24 vessels)
(Calibration Curve)
A quantitative value was calculated using the product of a GC-FPD quantitative value based on a carbon disulfide calibration curve with 5 concentrations (0.04, 0.1, 0.2, 0.4, and 0.8 μg/mL) and a dilution ratio of an extraction solvent to a specimen.
(Analysis Conditions)
The above measurement conditions were employed.
(Specimen)
Hochu-ekki-to (1.0 g each) was used as a specimen.
(Pesticides Added)
A propineb pesticide standard solution (20 μg/mL (in terms of carbon disulfide) solution) (100 μL) was added to each specimen. (2.0 μg/mL: concentration in terms of carbon disulfide in each specimen)
(Conditions for Pretreatment Test Solutions)
Cyclohexane (5.0 mL) and 30 mL of a 1% L-cysteine 1.5% tin chloride 5.0 mol/L hydrochloric acid solution were added and then 3 vessels were separately treated at the same time. Table 17 and Table 18 show the parameters based upon which the pretreatment method was carried out.

TABLE 17

| | time/ minute | Microwave Power Upper limit/W | Temperature/° C. | Stirrer Power/% |
|---|---|---|---|---|
| $1^{st}$ step | 5 | 600 | Room temperature→100 | 80 |
| $2^{nd}$ step | 5, 10, 15 | 300 | 100 | 80 |
| $3^{rd}$ step | 100 | 0 | 100→Room temperature | 80 |

TABLE 18

| | time/ minute | Microwave Power Upper limit/W | Temperature/° C. | Stirrer Power/% |
|---|---|---|---|---|
| $1^{st}$ step | 5 | 600 | Room temperature→100 | 80 |
| $2^{nd}$ step | 20, 25 | 300 | 100 | 80 |
| $3^{rd}$ step | 60 | 0 | 100→Room temperature | 80 |

(Results and Discussion)
Table 19 shows the results. Results of 5 to 20 minutes of digestion at 100° C. showed no significant difference in recovery percentage. Recovery percentage was found to slightly improve by about 5% in the case of 25 minutes of digestion. Twenty five (25) minutes of digestion at 100° C. means a total of 30 minutes of microwave heating. Hence, it was concluded that 10 minutes of digestion at 100° C. was preferable because of the relatively short heating time and the fact that it involved the least variation in data.

TABLE 19

| Specimen name | Digestion time (minute) | Recovery (%) | Average value, RSD (%) |
|---|---|---|---|
| Hochu-ekki-to | 5 | 76.6 | |
| | 5 | 81.2 | 80.0 |
| | 5 | 82.0 | 3.6 |
| Hochu-ekki-to | 10 | 82.7 | |
| | 10 | 81.4 | 81.9 |
| | 10 | 81.7 | 0.9 |
| Hochu-ekki-to | 15 | 85.1 | |
| | 15 | 82.4 | 83.1 |
| | 15 | 81.8 | 2.1 |
| Hochu-ekki-to | 20 | 74.3 | |
| | 20 | 82.6 | 79.3 |
| | 20 | 80.9 | 5.5 |
| Hochu-ekki-to | 25 | 85.6 | |
| | 25 | 86.1 | 85.4 |
| | 25 | 84.6 | 0.9 |

6. Confirmation of Actual Measured Values of Residual Pesticides in Contaminated Prescriptions
Comparison was carried out with actual measured data of contaminated samples from which dithiocarbamate pesticides had been detected by a method disclosed by the Ministry of the Environment (Guidelines for Testing Food Sanitation (Shokuhin Eisei Kensa Shishin), Volume of Residual Pesticide, p. 864).
(Reaction Vessel Capacity)
70 mL (simultaneous pretreatment of a maximum of 24 vessels)
(Calibration Curve)
A quantitative value was calculated using the product of GC-FPD quantitative value based on a carbon disulfide calibration curve with 5 concentrations (0.04, 0.1, 0.2, 0.4, and 0.8 μg/mL) and the dilution ratio of an extraction solvent to a specimen.
(Analysis Conditions)
The above measurement conditions were employed.
(Specimens)
A contaminated sample (1.0 g each) was used as a specimen.
(Conditions for Pretreatment Test Solutions)
Cyclohexane (5.0 mL), and 30 mL of a 1% L-cysteine 1.5% tin chloride 5.0 mol/L hydrochloric acid solution were added, and then 3 vessels were separately treated at the same time. Table 20 shows the parameters based upon which the pretreatment method was carried out.

TABLE 20

| | time/ minute | Microwave Power Upper limit/W | Temperature/° C. | Stirrer Power/% |
|---|---|---|---|---|
| $1^{st}$ step | 5 | 800 | Room temperature→100 | 80 |
| $2^{nd}$ step | 10 | 800 | 100 | 80 |
| $3^{rd}$ step | 75 | 0 | 100→Room temperature | 80 |

(Results and Discussion)
Table 21 shows the results. The data obtained by a microwave test method were almost equivalent to actual measured data obtained by the method disclosed by the Ministry of Environment and showed small variations. The data obtained by the microwave test method were somewhat lower than the data obtained by the method disclosed by the Ministry of Environment, but the data were acceptable since they satisfied the recovery percentage requirements (70% to 120%). Also, such results were inferred to have occurred due to quantitative errors near the minimum value within the calibration curve range. Based on these results and previous addition and recovery test results, it was concluded that the test method can sufficiently ensure accuracy required for a pesticide test method.

TABLE 21

| Test method | Sample name | Residue level (ppm) | Average value, RSD (%) |
|---|---|---|---|
| Microwave-assisted method | Contamination sample | 0.234 0.223 0.230 | 0.229 2.43 |
| Methods as disclosed by the Ministry of the Environment | Contamination sample | 0.286 | |

Example 2

An addition and recovery test was conducted for dithiocarbamate pesticides in ethical drugs, nonprescription drugs, and other products using a microwave carbon disulfide method.
1. Methods
(1) Instrumentation
Pretreatment Apparatus: Microwave-Assisted Solvent Extractor
ETHOS 1 (MILESTONE, microwave oven body, option: internal temperature sensor and magnetic stirrer)
PRO24 (MILESTONE, rotor for simultaneous treatment of 24 vessels)
Stirrer (diameter 6 mm×full length 20 mm)
Analyzer: GC-FPD (system recognition No. GC-7)
6890N (Agilent Technologies, main body)
7683 (Agilent Technologies, autosampler)
Inlets: split/splitless inlet
Inserts: split/splitless liner (Agilent Technologies, 5183-4711)
FPD detector (sulfur mode wavelength filter 393 nm)
(2) Reagent
Carbon disulfide (hereinafter, referred to as $CS_2$): Wako Pure Chemical Industries, Ltd., special grade reagent
Hydrochloric acid: Wako Pure Chemical Industries, Ltd., $1^{st}$ grade reagent
Tin (II) chloride dihydrate: Kanto Chemical Co., Inc., special grade reagent
L-cysteine hydrochloride monohydrate: Wako Pure Chemical Industries, Ltd., special grade reagent
Cyclohexane: Kanto Chemical Co., Inc., residual pesticide for PCB test or special grade reagent
Acetone: Kanto Chemical Co., Inc., residual pesticide for PCB test
Acetonitrile: Kanto Chemical Co., Inc., residual pesticide for PCB test
Distilled water (washed with hexane): Wako Pure Chemical Industries, Ltd., for testing residual pesticides
(3) Pesticide Reference Standard

| Pesticide reference standard name | Maker | Purity | $CS_2$ conversion factor |
|---|---|---|---|
| Thiuram | Wako Pure Chemical Industries, Ltd. | 100% | 1.58 |
| Zineb | Wako Pure Chemical Industries, Ltd. | 80.5% | 1.81 |
| Propineb | GL Sciences Inc. | 80% | 1.90 |
| Ziram | Wako Pure Chemical Industries, Ltd. | 97.7% | 2.01 |
| Organic nickel | GELEST Inc. | 100% | 1.97 |
| Ferbam | Wako Pure Chemical Industries, Ltd. | 99.3% | 1.82 |
| Maneb | Wako Pure Chemical Industries, Ltd. | 90.2% | 1.74 |

-continued

| Pesticide reference standard name | Maker | Purity | CS$_2$ conversion factor |
|---|---|---|---|
| Manzeb | Wako Pure Chemical Industries, Ltd. | 91% | 1.77 |
| Polycarbamate | Wako Pure Chemical Industries, Ltd. | 96% | 1.91 |

Purities are data published from the makers.

(4) Specimens

Ethical drugs: 128 prescriptions of ethical Kampo extract formulations, Nonprescription drugs and other products: OTC Kampo extract formulation (granules) 6 items, OTC non-Kampo crude drug product (granules) 2 items, OTC Kampo extract formulation (tablets) 6 items, OTC non-Kampo crude drug product (tablet) 2 items, and other 16 items (5) Preparation of Reagents Catalytic reagent: 1.55% tin (II) chloride-1% L-cysteine-5 mol/L hydrochloric acid Tin (II) chloride dihydrate (18.4 g) and 14.7 g of L-cysteine hydrochloride monohydrate were dissolved in 1000 mL of 5 mol/L hydrochloric acid.

(6) Preparation of CS$_2$ Standard Solutions for a Calibration Curve

Approximately 12 mL of cyclohexane was added to a 25-mL measuring flask and then the mass was accurately measured. One (1) mL of CS$_2$ was added to the flask, and then the mass was accurately measured again. The resultant was diluted with cyclohexane to prepare 25 mL of a standard stock solution. The solution was subjected to serial dilution with cyclohexane. Thus, standard solutions 1-5 (approximately 0.8, 0.4, 0.2, 0.1, and 0.04 µg/mL) were prepared.

The accurate concentration of each standard solution was calculated based on the accurate mass of 1 mL of CS$_2$.

(7) Preparation of a Pesticide Reference Standard Solution for Examination of Recovery Percentage A pesticide reference standard solution was prepared so that the concentration (in terms of CS$_2$) was 20 µg/mL, according to the following table.

The accurate concentration (in terms of CS$_2$) in a pesticide reference standard solution was calculated according to the following formula using the accurate mass and purity of a weighed reference standard and CS$_2$ conversion factor.

Concentration (in terms of CS$_2$) (µg/mL)=concentration of pesticide reference standard (µg/mL)×purity÷CS$_2$ conversion factor (8) Pretreatment for Samples A digestion vessel was directly placed on a balance to accurately weigh a specimen, a stirrer was placed in the vessel, and then the vessel was closed. A pesticide standard solution (100 µL) was added to the vessel using a dispenser pipette, so that the concentration of a pesticide in the specimen became a value of standard for a preparation, 2 ppm (in terms of CS$_2$). Subsequently, 5 mL of cyclohexane was added using a dispenser pipette. A catalytic reagent (30 mL) was then added thereto using a dispenser, the vessel was placed in a pressure container, and then the safety valve was closed. Similar procedures were carried out for the number of vessels to be subjected to measurement. A single pressure container was assembled, in which an internal temperature sensor had been separately installed. The pressure containers were arranged in a circularly symmetrical manner with respect to the rotor body and then covered. An internal temperature sensor probe was then attached, and then the pressure containers were positioned in the oven body. Then, digestion and extraction were carried out by the following pretreatment method.

After digestion and extraction, the pressure containers were removed and then the safety valves were opened. Each digestion vessel was removed and uncovered and then a cyclohexane layer was sampled in a vial for measurement using a Pasteur pipette.

| Pesticide name | Solvent | Amount of pesticide weighed | Volume prepared |
|---|---|---|---|
| Thiuram | Acetone (Kanto Chemical Co., Inc.) | 3.16 mg | 100 mL |
| Zineb | Acetonitrile (Kanto Chemical Co., Inc.) | 4.50 mg | 100 mL |
| Propineb | Distilled water-washed with hexane (Wako Pure Chemical Industries, Ltd.) | 4.75 mg | 100 mL |
| Ziram | Acetone (Kanto Chemical Co., Inc.) | 4.11 mg | 100 mL |
| Organic nickel | Distilled water-washed with hexane (Wako Pure Chemical industries, Ltd.) | 3.94 mg | 100 mL |
| Ferbam | Acetone (Kanto Chemical Co., Inc.) | 3.67 mg | 100 mL |
| Maneb | Acetonitrile (Kanto Chemical Co., Inc.) | 3.86 mg | 100 mL |
| Manzeb | Distilled water-washed with hexane (Wako Pure Chemical Industries, Ltd.) | 3.89 mg | 100 mL |
| Polycarbamate | Acetonitrile (Kanto Chemical Co., Inc.) | 3.98 mg | 100 mL |

To find an actual measured value of a dithiocarbamate pesticide in a specimen, pretreatment similar to the above was carried out without adding any pesticide reference standard solution.

<Pretreatment Apparatus Method 1>
Stirrer power: 80%
Rotor rotation: ON
Temperature control within digestion vessel: room temperature →100° C./5 min→100° C. (hold for 10 minutes)
Air-cooling time after reaction: 75 minutes
<Pretreatment apparatus method 2>
Stirrer power: 80%
Rotor rotation: ON
Temperature control within digestion vessel: room temperature →90° C./7 min→90° C. (hold for 10 minutes)
Air-cooling time after reaction: 73 minutes
(9) GC-FPD Measurement Conditions:
Same as in Example 1.
(10) Preparation of a Calibration Curve The $CS_2$ standard solutions, 1-5 for a calibration curve were each analyzed once by GC-FPD. Linear regression was carried out by a least square method based on the common logarithm (yi) of peak area value (y) with respect to the common logarithm (xi) of $CS_2$ concentration (x), so that a calibration curve was prepared.

(11) Calculation of Concentrations in Analytical Samples and Handling of Numerical Values The common logarithm (Yi) of peak area value (Y) of $CS_2$ was found. The concentration of a pesticide (X ppm in terms of $CS_2$) was calculated by the following calculation method using Slope "a" and yi intercept "h" in primary formula yi=a Xi+b of the calibration curve.

$$X(\text{ppm}) = 10^{(yi-b/a)} \times 5$$

(correction coefficient=5, since 5 mL of cyclohexane was added per gram of a preparation)

Recovery percentage was found by calculating the concentration of a pesticide in an analytical sample as a percentage relative to the accurate concentration (in terms of $CS_2$) in a pesticide reference standard solution added. Upon measurement with N=1, recovery figures were rounded off to the first decimal place. Upon measurement with N=3, recovery figures were truncated to two decimal places, and then average or relative standard deviation (RSD) was rounded off to the first decimal place.

2. Results
Addition and Recovery Test

An addition and recovery test of ethical Kampo extract formulations was conducted as follows. Concerning 20 prescriptions, the test was conducted with N=3 for thiuram, zineb, and propineb. Furthermore, regarding Toki-shakuyaku-san, Hochu-ekki-to, and Dai-kenchu-to, the test was also conducted for ziram, organic nickel, ferbam, maneb, manzeb, and polycarbamate therein (N=3). Concerning prescriptions other than the aforementioned prescriptions, the test was conducted with N=1, for thiuram, zineb, and propineb.

Table 22 shows recovery percentages for thiuram, zineb, and propineb in 128 prescriptions of ethical Kampo extract formulations.

TABLE 22

| Prescription | | Recovery (%) | | | | | |
|---|---|---|---|---|---|---|---|
| No. | Prescription name | Thiuram | RSD | Zineb | RSD | Propineb | RSD |
| 23 | Toki-shakuyaku-san | 104.9 | 4.0 | 93.2 | 8.1 | 78.4 | 6.0 |
| 41 | Hochu-ekki-to | 106.0 | 1.7 | 102.8 | 1.1 | 87.9 | 2.2 |
| 100 | Dai-kenchu-to | 94.4 | 3.8 | 94.6 | 4.7 | 81.5 | 3.5 |
| 2 | Kakkon-to-ka-senkyu-shin'i | 105.9 | 2.5 | 101.8 | 3.1 | 89.0 | 9.1 |
| 6 | Jumi-haidoku-to | 107.2 | 2.2 | 100.5 | 1.0 | 91.0 | 1.7 |
| 16 | Hange-koboku-to | 106.8 | 1.8 | 91.5 | 4.0 | 86.8 | 1.3 |
| 37 | Hange-byakujutsu-temma-to | 113.2 | 4.7 | 91.8 | 1.9 | 91.2 | 7.3 |
| 43 | Rikkunshi-to | 103.7 | 3.7 | 101.9 | 4.4 | 86.9 | 3.0 |
| 47 | Choto-san | 111.4 | 2.2 | 106.6 | 0.7 | 86.7 | 6.5 |
| 48 | Juzen-taiho-to | 100.8 | 3.7 | 95.6 | 4.8 | 78.8 | 1.1 |
| 50 | Keigai-rengyo-to | 108.7 | 6.1 | 98.7 | 2.5 | 78.3 | 7.4 |
| 51 | Juncho-to | 107.0 | 3.6 | 92.5 | 2.8 | 76.4 | 3.4 |
| 53 | Sokei-kakketsu-to | 108.0 | 5.6 | 76.0 | 2.8 | 80.8 | 2.3 |
| 54 | Yoku-kan-san | 101.2 | 5.3 | 83.8 | 3.9 | 85.2 | 0.9 |
| 58 | Seijo-bofu-to | 105.2 | 7.9 | 97.7 | 4.7 | 82.3 | 3.1 |
| 62 | Bofu-tsusho-san | 109.9 | 3.1 | 104.4 | 1.4 | 86.0 | 1.1 |
| 96 | Saiboku-to | 109.0 | 2.5 | 116.4 | 3.7 | 87.6 | 6.0 |
| 106 | Unkei-to | 112.1 | 4.5 | 118.0 | 1.6 | 89.1 | 2.5 |
| 108 | Ninjin-yoei-to | 118.3 | 3.9 | 110.3 | 4.6 | 82.2 | 1.2 |
| 126 | Mashinin-gan | 107.6 | 2.5 | 98.9 | 3.6 | 83.2 | 3.2 |
| 1 | Kakkon-to | 84.4 | | 111.7 | | 89.9 | |
| 3 | Otsuji-to | 96.3 | | 106.3 | | 86.2 | |
| 5 | Anchu-san | 99.7 | | 96.8 | | 81.3 | |
| 7 | Hachimi-jio-gan | 76.7 | | 102.9 | | 84.3 | |
| 8 | Dai-saiko-to | 89.3 | | 89.8 | | 95.9 | |
| 9 | Sho-saiko-to | 94.1 | | 107.2 | | 86.4 | |
| 10 | Saiko-keishi-to | 96.7 | | 109.3 | | 86.4 | |
| 11 | Saiko-keishi-kankyo-to | 99.2 | | 98.1 | | 74.3 | |
| 12 | Saiko-ka-ryukotsu-borei-to | 92.8 | | 105.2 | | 74.0 | |
| 14 | Hange-shashin-to | 98.7 | | 112.5 | | 100.6 | |
| 15 | Oren-gedoku-to | 96.1 | | 102.1 | | 85.9 | |
| 17 | Gorei-san | 96.8 | | 93.0 | | 84.0 | |
| 18 | Keishi-ka-jutsu-bu-to | 100.6 | | 107.2 | | 91.5 | |
| 19 | Sho-seiryu-to | 93.7 | | 113.1 | | 100.7 | |
| 20 | Boi-ogi-to | 91.8 | | 100.6 | | 83.6 | |
| 21 | Sho-hange-ka-bukuryo-to | 100.0 | | 107.4 | | 89.5 | |
| 22 | Shofu-san | 105.8 | | 97.1 | | 78.4 | |
| 24 | Kami-shoyo-san | 112.9 | | 103.7 | | 85.4 | |

TABLE 22-continued

| Prescription | | Recovery (%) | | | | | |
|---|---|---|---|---|---|---|---|
| No. | Prescription name | Thiuram | RSD | Zineb | RSD | Propineb | RSD |
| 25 | Keishi-bukuryo-gan | 117.3 | | 106.4 | | 78.8 | |
| 26 | Keishi-ka-ryukotsu-borei-to | 116.9 | | 89.0 | | 79.7 | |
| 27 | Mao-to | 99.1 | | 95.0 | | 75.0 | |
| 28 | Eppi-ka-jutsu-to | 113.4 | | 86.0 | | 74.9 | |
| 29 | Bakumondo-to | 111.1 | | 99.9 | | 86.0 | |
| 30 | Shimbu-to | 104.5 | | 93.3 | | 71.8 | |
| 31 | Goshuyu-to | 117.1 | | 91.6 | | 77.5 | |
| 32 | Ninjin-to | 109.2 | | 98.6 | | 73.9 | |
| 33 | Daio-botampi-to | 109.9 | | 89.4 | | 77.0 | |
| 34 | Byakko-ka-ninjin-to | 108.5 | | 95.2 | | 76.6 | |
| 35 | Shigyaku-san | 112.6 | | 88.8 | | 73.6 | |
| 36 | Moku-boi-to | 107.5 | | 100.5 | | 77.0 | |
| 38 | Toki-shigyaku-ka-goshuyu-shokyo-to | 88.2 | | 96.0 | | 84.6 | |
| 39 | Ryo-kei-jutsu-kan-to | 92.6 | | 77.2 | | 78.0 | |
| 40 | Chorei-to | 91.6 | | 99.2 | | 85.1 | |
| 45 | Keishi-to | 99.7 | | 107.3 | | 80.9 | |
| 46 | Shichimotsu-koka-to | 85.3 | | 72.3 | | 79.5 | |
| 52 | Yokuinin-to | 94.8 | | 74.2 | | 74.3 | |
| 55 | Ma-kyo-kan-seki-to | 91.0 | | 97.4 | | 74.4 | |
| 56 | Gorin-san | 93.5 | | 94.1 | | 74.0 | |
| 57 | Unsei-in | 90.8 | | 99.5 | | 71.2 | |
| 59 | Ji-zuso-ippo | 96.3 | | 94.5 | | 81.7 | |
| 60 | Keishi-ka-shakuyaku-to | 98.7 | | 95.7 | | 74.5 | |
| 61 | Tokaku-joki-to | 92.2 | | 93.4 | | 80.1 | |
| 63 | Goshaku-san | 90.1 | | 92.8 | | 82.6 | |
| 64 | Sha-kanzo-to | 95.1 | | 91.3 | | 82.9 | |
| 65 | Kihi-to | 102.9 | | 85.7 | | 78.8 | |
| 66 | Jinso-in | 93.3 | | 92.5 | | 87.2 | |
| 67 | Nyoshin-san | 94.3 | | 82.8 | | 81.3 | |
| 68 | Shakuyaku-kanzo-to | 94.2 | | 90.0 | | 77.5 | |
| 69 | Bukuryo-in | 94.7 | | 82.9 | | 74.9 | |
| 70 | Koso-san | 93.0 | | 89.7 | | 78.3 | |
| 71 | Shimotsu-to | 84.8 | | 85.3 | | 74.7 | |
| 72 | Kam-baku-taiso-to | 88.4 | | 94.1 | | 81.5 | |
| 73 | Saikan-to | 88.3 | | 85.6 | | 87.5 | |
| 74 | Choi-joki-to | 100.2 | | 80.9 | | 82.4 | |
| 75 | Shikunshi-to | 97.2 | | 94.1 | | 80.7 | |
| 76 | Ryutan-shakan-to | 94.5 | | 90.3 | | 78.4 | |
| 77 | Kyuki-kyogai-to | 95.1 | | 70.3 | | 78.8 | |
| 78 | Ma-kyo-yoku-kan-to | 103.3 | | 73.0 | | 82.4 | |
| 79 | Heii-san | 95.1 | | 96.9 | | 71.5 | |
| 80 | Saiko-seikan-to | 89.6 | | 72.4 | | 78.3 | |
| 81 | Nichin-to | 101.3 | | 76.8 | | 85.6 | |
| 82 | Keishi-ninjin-to | 104.0 | | 98.0 | | 75.0 | |
| 83 | Yoku-kan-san-ka-chimpi-hange | 98.2 | | 73.4 | | 78.8 | |
| 84 | Daio-kanzo-to | 97.8 | | 89.5 | | 76.1 | |
| 85 | Shimpi-to | 102.2 | | 101.9 | | 72.7 | |
| 86 | Toki-inshi | 98.9 | | 98.3 | | 71.6 | |
| 87 | Rokumi-gan | 85.2 | | 98.4 | | 78.9 | |
| 88 | Nijutsu-to | 103.2 | | 100.9 | | 73.3 | |
| 89 | Ji-daboku-ippo | 104.8 | | 97.3 | | 76.8 | |
| 90 | Seihai-to | 97.5 | | 97.3 | | 75.1 | |
| 91 | Chikujo-untan-to | 108.5 | | 111.9 | | 76.4 | |
| 92 | Jiin-shiho-to | 108.1 | | 108.0 | | 74.1 | |
| 93 | Jiin-koka-to | 107.3 | | 103.0 | | 77.9 | |
| 95 | Goko-to | 115.9 | | 107.5 | | 78.0 | |
| 97 | Dai-bofu-to | 104.6 | | 82.7 | | 78.1 | |
| 98 | Ogi-kenchu-to | 98.6 | | 97.7 | | 72.1 | |
| 99 | Sho-kenchu-to | 101.1 | | 103.7 | | 73.2 | |
| 101 | Shoma-kakkon-to | 99.6 | | 102.7 | | 75.1 | |
| 102 | Toki-to | 87.2 | | 90.0 | | 70.5 | |
| 103 | Sansonin-to | 97.4 | | 89.9 | | 72.5 | |
| 104 | Shin'i-seihai-to | 89.1 | | 99.9 | | 76.9 | |
| 105 | Tsu-do-san | 104.8 | | 98.2 | | 82.2 | |
| 107 | Gosha-jinki-gan | 89.1 | | 89.4 | | 82.1 | |
| 109 | Sho-saiko-to-ka-kikyo-sekko | 98.6 | | 110.4 | | 82.9 | |
| 110 | Rikko-san | 108.4 | | 106.6 | | 76.9 | |
| 111 | Seishin-renshi-in | 110.4 | | 97.8 | | 78.4 | |

TABLE 22-continued

| Prescription No. | Prescription name | Recovery (%) Thiuram | RSD | Zineb | RSD | Propineb | RSD |
|---|---|---|---|---|---|---|---|
| 112 | Chorei-to-go-shimotsu-to | 113.3 | | 103.0 | | 77.9 | |
| 113 | San'o-shashin-to | 111.9 | | 108.6 | | 78.9 | |
| 114 | Sairei-to | 111.2 | | 106.2 | | 76.3 | |
| 115 | Irei-to | 119.9 | | 82.7 | | 71.7 | |
| 116 | Bukuryo-in-go-hange-koboku-to | 80.7 | | 99.5 | | 77.4 | |
| 117 | Inchin-gorei-san | 99.2 | | 82.8 | | 72.8 | |
| 118 | Ryo-kyo-jutsu-kan-to | 107.9 | | 102.2 | | 80.7 | |
| 119 | Ryo-kan-kyo-mi-shin-ge-nin-to | 91.7 | | 104.2 | | 70.2 | |
| 120 | Oren-to | 96.3 | | 104.0 | | 74.9 | |
| 121 | Sammotsu-ogon-to | 96.6 | | 86.2 | | 75.5 | |
| 122 | Haino-san-kyu-to | 101.9 | | 107.2 | | 80.2 | |
| 123 | Toki-kenchu-to | 103.1 | | 115.3 | | 74.0 | |
| 124 | Senkyu-chacho-san | 104.9 | | 99.9 | | 73.4 | |
| 125 | Keishi-bukuryo-gan-ka-yokuinin | 106.8 | | 113.5 | | 82.2 | |
| 127 | Mao-bushi-saishin-to | 101.7 | | 90.4 | | 78.3 | |
| 128 | Keihi-to | 90.0 | | 100.4 | | 75.7 | |
| 133 | Dai-joki-to | 101.8 | | 95.8 | | 81.3 | |
| 134 | Keishi-ka-shakuyaku-daio-to | 95.2 | | 112.5 | | 71.6 | |
| 135 | Inchinko-to | 96.6 | | 72.8 | | 77.4 | |
| 136 | Seisho-ekki-to | 99.2 | | 95.5 | | 80.6 | |
| 137 | Kami-kihi-to | 100.4 | | 87.8 | | 71.0 | |
| 138 | Kikyo-to | 100.9 | | 108.9 | | 84.0 | |

Recovery percentages ranging from 70% to 120% were achieved in all prescriptions. In the case of contaminated prescriptions, the actual measured concentration of a dithiocarbamate pesticide in the specimen was 0.23 μg/mL. Hence, the recovery percentages were corrected using the actual measured value, so that the recovery percentages ranged from 70% to 120%.

Table 23 shows the recovery percentages for ziram, organic nickel, ferbam, maneb, manzeb, and polycarbamate in Toki-shakuyaku-san, Hochu-ekki-to, and Dai-kenchu-to.

TABLE 23

| Prescription No. | Prescription name | Ziram | RSD | Organic Ni | RSD | Ferbam | RSD |
|---|---|---|---|---|---|---|---|
| 23 | Toki-shakuyaku-san | 89.2 | 7.0 | 85 | 2.1 | 87.0 | 8.2 |
| 41 | Hochu-ekki-to | 103.8 | 1.7 | 98.5 | 3.7 | 100.5 | 2.2 |
| 100 | Dai-kenchu-to | 95.8 | 6.0 | 89.8 | 5.3 | 90.6 | 3.0 |

| Prescription No. | Prescription name | Maneb | RSD | Manzeb | RSD | Polycarbamate | RSD |
|---|---|---|---|---|---|---|---|
| 23 | Toki-shakuyaku-san | 112.3 | 6.5 | 88.0 | 7.2 | 87.7 | 9.8 |
| 41 | Hochu-ekki-to | 84.9 | 4.8 | 91.9 | 3.4 | 110.9 | 5.8 |
| 100 | Dai-kenchu-to | 116.8 | 5.1 | 100.8 | 2.5 | 103.7 | 9.7 |

Recovery percentages ranging from 70% to 120% were achieved for all pesticides in specimens. Also, variation (RSD) in recovery percentages was within 10%.

Table 24 shows the recovery percentages for thiuram, zineb, and propineb in the "TSUMURA" Tokon (ipecac) syrup.

TABLE 24

| Product code.product name | Recovery (%) Thiuram | Zineb | Propineb |
|---|---|---|---|
| "TSUMURA" Tokon (Ipecac) syrup | 88.4 | 97.6 | 84.3 |

The recovery percentages in the case of the "TSUMURA" Tokon (ipecac) syrup satisfied the criterion.

Table 25 shows the recovery percentages for thiuram, zineb, and propineb in nonprescription drugs and other products.

TABLE 25

| Product code.product name | Recovery (%) Thiuram | Zineb | Propineb |
|---|---|---|---|
| N-001 (Kakkon-to granules) | 105.0 | 82.5 | 84.8 |
| N-007 (Hachimi-jio-gan granules) | 92.3 | 102.6 | 101.7 |
| N-010 (Saiko-keishi-to granules) | 116.7 | 107.5 | 103.7 |

TABLE 25-continued

| Product code.product name | Recovery (%) | | |
|---|---|---|---|
| | Thiuram | Zineb | Propineb |
| N-015 (Oren-gedoku-to granules) | 112.6 | 105.7 | 108.1 |
| N-017 (Gorei-san granules) | 92.4 | 100.7 | 94.4 |
| N-025 (Keishi-bukuryo-gan granules) | 111.9 | 96.7 | 104.5 |
| Kampofrau | 105.0 | 94.0 | 100.2 |
| KampoAsthma | 111.4 | 112.2 | 103.7 |
| PT-001 (Kakkon-to tablets) | 98.0 | 98.6 | 81.0 |
| PT-010 (Saiko-keishi-to) | 107.7 | 107.5 | 86.2 |
| PT-019 (Sho-seiryu-to tablets) | 104.8 | 101.2 | 89.2 |
| PT-023 (Toki-shakuyaku-san tablets) | 106.0 | 103.4 | 80.7 |
| PT-024 (Kami-shoyo-san tablets) | 102.1 | 102.2 | 84.5 |
| PT-025 (Keishi-bukuryo-gan tablets) | 99.8 | 103.5 | 78.9 |
| L'amour Q uncoated tablets | 97.6 | 102.2 | 77.9 |
| Chujo-to L'amour uncoated tablets | 112.3 | 102.9 | 78.0 |
| Kikyo-to troches | 97.9 | 103.4 | 82.6 |
| Kakkon-to liquid for internal use (for elementary and junior high schoolers) | 99.4 | 85.8 | 82.5 |
| Kakkon-to liquid for internal use | 92.2 | 84.1 | 73.3 |
| Sho-seiryu-to liquid for internal use | 96.2 | 92.4 | 76.6 |
| Saiko-keishi-to liquid for internal use | 96.7 | 92.7 | 75.3 |
| Bakumondo-to liquid for internal use | 90.6 | 89.7 | 84.1 |
| Mao-to liquid for internal use | 93.8 | 96.5 | 76.7 |
| Saiko-ka-ryukotsu-borei-to liquid for internal use | 95.3 | 84.5 | 72.8 |
| Daio-kanzo-to liquid for internal use | 85.1 | 80.2 | 73.3 |
| Digestive medicine in the form of liquid for internal use | 99.0 | 94.8 | 86.2 |
| Haikutan D | 98.1 | 90.0 | 83.0 |
| Haikutan gold | 75.2 | 100.5 | 78.3 |
| Haikutan ace 50 | 103.1 | 79.3 | 83.7 |
| WantenPα | 109.4 | 107.7 | 104.0 |
| Yu-tan-gan | 111.1 | 109.6 | 87.3 |
| Kudzu gruel | 111.0 | 105.8 | 104.1 |

Regardless of the forms of preparations (granules, solids, or liquids), it was confirmed that the criterion (that is, recovery percentages ranging from 70% to 120%) was achieved for all products other than yu-tan-gan. In the case of yu-tan-gan, the recovery percentage for zineb or thiuram exceeded 120%, but the actual measured concentration of the dithiocarbamate pesticide in the specimen was 0.29 μg/mL. When correction using the actual measured value was carried out, the recovery percentages were within 120%. At this time, the recovery percentages for propineb were 70% or more.

INDUSTRIAL APPLICABILITY

The present invention is used as a method for analyzing dithiocarbamate pesticides existing in crude drugs or preparations containing the same.

The invention claimed is:

1. A method for analyzing a dithiocarbamate pesticide, comprising adding a crude drug, a preparation containing the crude drug, or a treated product thereof, L-cysteine or a salt thereof, and an organic solvent for extraction to a reaction vessel, sealing the reaction vessel, carrying out microwave irradiation, digesting a dithiocarbamate pesticide existing in the crude drug or the preparation containing the same into carbon disulfide, carrying out fractional extraction using the organic solvent, and then analyzing the extract.

2. The method according to claim 1, further comprising adding an aqueous acid catalyst solution to said reaction vessel and then sealing said reaction vessel.

3. The method according to claim 2, wherein the aqueous acid catalyst solution contains tin (II) chloride or a hydrate thereof and hydrochloric acid.

4. The method according to claim 1, wherein the organic solvent for extraction is cyclohexane or 2,2,4-trimethylpentane.

5. The method according to claim 1, whereby the analysis of the extract is conducted using a gas chromatograph.

6. The method according to claim 1, wherein the dithiocarbamate pesticide contains propineb.

7. The method according to claim 1, wherein the crude drug or the preparation containing the crude drug is a kampo preparation, a dietary supplement, a quasi-drug, or a cosmetic.

8. The method according to claim 1, which employs as L-cysteine or a salt thereof an aqueous solution of L-cysteine or a salt thereof having a concentration of from 0.1 w/v % to 10.0 w/v %.

9. The method according to claim 1, which employs as L-cysteine or a salt thereof an aqueous solution of L-cysteine or a salt thereof having a concentration of from 2.0 w/v % to 6.0 w/v %.

10. The method according to claim 1, which employs as L-cysteine or a salt thereof an aqueous solution of L-cysteine or a salt thereof having a concentration of 4.0 w/v %.

11. The method according to claim 1, further comprising:
preparing an aqueous solution in advance by mixing tin (II) chloride or a hydrate thereof, hydrochloric acid, and water,
adding the obtained aqueous solution to the reaction vessel; and
sealing the vessel.

12. The method according to claim 11, wherein a concentration of hydrochloric acid in the aqueous solution ranges from 0.5 mol/L to 6.0 mol/L, and a concentration of tin (II) chloride or a hydrate thereof in the same ranges from 0.1 w/v % to 5.0 w/v %.

13. The method according to claim 11, wherein, said aqueous solution prepared in advance further comprises L-cysteine or a salt thereof and a concentration of L-cysteine or a salt thereof in the aqueous solution ranges from 0.1 w/v % to 5.0 w/v %.

14. The method according to claim 1, wherein:
1 g to 5 g of the crude drug, the preparation containing the crude drug, or the treated product thereof, is added to the reaction vessel,
10 mL to 30 mL of (i) an aqueous acid catalyst solution containing L-cysteine or a salt thereof or (ii) an aqueous solution containing L-cysteine or a salt thereof, is added to the reaction vessel,
and
5 mL to 20 mL of an organic solvent for extraction, is added to the reaction vessel.

15. The method according to claim 1, wherein the microwave irradiation is carried out via the following 3 steps:
1st step: to keep the temperature of a reaction solution in the reaction vessel between 80° C. and 100° C., the microwave power is increased upon initiation of the microwave irradiation, so as to immediately raise the temperature;
2nd step: when the temperature of the solution reaches the above range, the microwave power is controlled to a degree such that the temperature can be maintained and then irradiation is carried out for required time length; and
3rd step: after completion of the microwave irradiation, the temperature of the reaction solution is lowered to room temperature.

16. The method according to claim 1, which does not employ an aqueous acid catalyst solution.

17. The method according to claim 1, that does not employ tin (II) chloride or a hydrate thereof and hydrochloric acid.

18. The method according to claim 1, wherein the crude drug is selected from the group consisting of Japanese Angelica Root, Cnidium Rhizome, Moutan Bark, Bitter Orange Peel (Tohi), Citrus Unshiu Peel, Pinellia Tuber, Bupleurum Root, Asiasarum Root, Dioscorea Rhizome, Polygala Root, Jujube, Immature Orange, Schisandra Fruit, Achyranthes Root, Ophiopogon Tuber, Angelica Dahurica Root, Perilla Herb, Zanthoxylum Fruit, Common Wheat Seed, Loquat Leaf, Peony Root, Cinnamon Bark, Poria Sclerotium, Cyperus Rhizome, Peach Kernel, Glycyrrhiza, Coptis Rhizome, Ginger, Clove, Corydails Tuber, Pueraria Root, Glehnia Root, Astragalus Root, Scutellaria Root, Platycodon Root, Rhubarb, Sinomenium Stem, Saposhnikovia Root, Phellodendron Bark, Magnolia Bark, Mentha Herb, Ephedra Herb, Schizonepeta Spike, Fennel, Evodia Fruit, Gardenia Fruit, Trichosanthes Seed, Apricot Kernel, Burdock Fruit, Jujube Seed, Plantago Seed, Sesame, Benincasa Seed, Coix Seed, Magnolia Flower, Gelatin, Cicada Periostracum, Trichosanthes Root, Araliae Cordata Root, Sophora Root, Processed Ginger, Peucedanum Root, Anemarrhena Rhizome, Gastrodia Tuber, Asparagus Tuber, Aralia Rhizome, Atractylodes Rhizome, Saussurea Root, Cimicifuga Rhizome, Japanese Valerian (Kissokon), Clematis Root, Senna Leaf (Senna), Artemisia Capillaris Flower, Artemisia Leaf, Uncaria Hook, Lycium Bark, Quercus Bark, Cornus Fruit, Hemp Fruit, Forsythia Fruit, Longan Aril, Polyporus Sclerotium, Areca, Malt, Amomum Seed, Brown Rice, Akebia Stem, Chrysanthemum Flower, Alpinia Officinarum Rhizome, Nelumbo Seed, Safflower, Lonicera Leaf and Stem, Tribulus Fruit, Polygonum Root, Bamboo Trunk, Nuphar Rhizome, Mulberry Bark, Arisaema Tuber, Sappan Wood, Fritillaria Bulb, Notopterigum, Lilium Bulb, Lithospermum Root, Processed Aconite Root, Eucommia Bark, Crataegus Fruit, Prepared Rehmannia Root (Jukujio), Ipecac (Tokon), Maltose, Panax Japonicus Rhizome (Chikusetsuninjin), Atractylodes Lancea Rhizome, Alisma Rhizome, Rehmannia Root, Ginseng, and Japanese Gentian.

19. The method according to claim 1, wherein the crude drug is selected from the group consisting of Japanese Angelica Root, Cnidium Rhizome, Moutan Bark, Bitter Orange Peel (Tohi), Citrus Unshiu Peel, Pinellia Tuber, Bupleurum Root, Asiasarum Root, Dioscorea Rhizome, Polygala Root, Jujube, Immature Orange, Schisandra Fruit, Achyranthes Root, Ophiopogon Tuber, Angelica Dahurica Root, Perilla Herb, Zanthoxylum Fruit, Common Wheat Seed, Loquat Leaf, Peony Root, Cinnamon Bark, Poria Sclerotium, Cyperus Rhizome, Peach Kernel, Glycyrrhiza, Coptis Rhizome, Ginger, Clove, Corydails Tuber, Pueraria Root, Glehnia Root, Astragalus Root, Scutellaria Root, Platycodon Root, Rhubarb, Sinomenium Stem, Saposhnikovia Root, Phellodendron Bark, Magnolia Bark, Mentha Herb, Ephedra Herb, Schizonepeta Spike, Fennel, Evodia Fruit, Gardenia Fruit, Trichosanthes Seed, Apricot Kernel, Burdock Fruit, Jujube Seed, Plantago Seed, Sesame, Benincasa Seed, Coix Seed, Magnolia Flower, Gelatin, Cicada Periostracum, Trichosanthes Root, Araliae Cordata Root, Sophora Root, Processed Ginger, Peucedanum Root, Anemarrhena Rhizo Me, Gastrodia Tuber, Asparagus Tuber, Aralia Rhizome, Atractylodes Rhizome, Saussurea Root, Cimicifuga Rhizome, Japanese Valerian (Kissokon), Clematis Root, Senna Leaf (Senna), Artemisia Capillaris Flower, Artemisia Leaf, Uncaria Hook, Lycium Bark, Quercus Bark, Cornus Fruit, Hemp Fruit, Forsythia Fruit, Longan Aril, Polyporus Sclerotium, Areca, Malt, Amomum Seed, Brown Rice, Akebia Stem, Chrysanthemum Flower, Alpinia Officinarum Rhizome, Nelumbo Seed, Safflower, Lonicera Leaf and Stem, Tribulus Fruit, Polygonum Root, Bamboo Trunk, Nuphar Rhizome, Mulberry Bark, Arisaema Tuber, Sappan Wood, Fritillaria Bulb, Notopterigum, Lilium Bulb, Lithospermum Root, Processed Aconite Root, Eucommia Bark, Crataegus Fruit, Prepared Rehmannia Root (Jukujio), Ipecac (Tokon), Maltose, and Panax Japonicus Rhizome (Chikusetsuninjin).

* * * * *

UNITED STATES PATENT AND TRADEMARK OFFICE
CERTIFICATE OF CORRECTION

PATENT NO. : 8,129,192 B2
APPLICATION NO. : 12/670295
DATED : March 6, 2012
INVENTOR(S) : Takahiro Toyoshima et al.

It is certified that error appears in the above-identified patent and that said Letters Patent is hereby corrected as shown below:

Please correct the following:

a) Column 41, line 2, in claim 14,

"1g to 5g of the crude drug," should read
-- 0.1g to 5g of the crude drug, -- b) Column 42, line 35, in claim 19,

"Anemarrhena Rhizo Me," should read
-- Anemarrhena Rhizome, --

Signed and Sealed this
Twenty-eighth Day of August, 2012

David J. Kappos
*Director of the United States Patent and Trademark Office*